(12) United States Patent
Wong et al.

(10) Patent No.: US 7,767,196 B2
(45) Date of Patent: Aug. 3, 2010

(54) OPTIMIZED RELAXIVITY AND SPECIFICITY HEPATOBILIARY MRI CONTRAST AGENT

(75) Inventors: Wing Tak Wong, Hong Kong (HK); Wai Yan Chan, Hong Kong (HK)

(73) Assignee: The University of Hong Kong, Hong Kong (HK)

( * ) Notice: Subject to any disclaimer, the term of this patent is extended or adjusted under 35 U.S.C. 154(b) by 929 days.

(21) Appl. No.: 11/601,011

(22) Filed: Nov. 17, 2006

(65) Prior Publication Data
US 2007/0116648 A1 May 24, 2007

Related U.S. Application Data

(60) Provisional application No. 60/738,102, filed on Nov. 21, 2005.

(51) Int. Cl.
*A61K 49/00* (2006.01)
*A61K 49/10* (2006.01)
(52) U.S. Cl. .................................. 424/9.35; 424/9.364
(58) Field of Classification Search ................. 424/9.1, 424/9.3, 9.35, 9.363, 1.65
See application file for complete search history.

(56) References Cited

U.S. PATENT DOCUMENTS

2004/0037777 A1 2/2004 Brechbiel et al.

OTHER PUBLICATIONS

I. Solomon, *Relaxation Prcesses in a System of Two Spins*, Phys, Rev., 1955, 99, 55.
N. Bloembergen, *Proton Relaxation Times in Paramagnetic Solutions*, J. Chem.Phys., 1957, 27, 257.
I. Solomon and N. Bloembergen, *Nuclear Magnetic Interactions in the HF Molecule*, J.Chem.Phys., 1956, 25, 261.
K. Raymond et al., *In Vivo Evaluation of Gadolinium Hydroxypyridonate Chelates: Initial Experience as Contrast Media in Magnetic Resonance Imaging*, J.Med.Chem., 2005, ASAP Article is updated as Thomson et al., J.Med.Chem., 2005, 48, 3874.
H. Kobayashi, *Macromolecular MRI Contast Agents with Small Dendrimers: Pharmacokinetic Differences Between Sizes and Cores*, Bioconjugate Chem., 2003, 14, 388.
N. Sato et al., *Pharmacokinetics and Enhancement Patterns of Macromolecular MR Contrast Agents With Various Sizes of Polyamidoamine Dendrimer Cores*, Magn.Reson.Med., 2001, 46, 1169.
S. Cohen et al., *Synthesis and Relaxation Properties of Mixed Gadolinium Hydroxypyridinonate MRI Contrast Agents*, Inorg. Chem., 2000, 39, 5747.
D. Meyer et al., *Advances in Macrocyclic Galolinium Complexes as Magnetic Resonance Imaging Contrast Agents*, Invest. Radiol., 1990, 25, S53.
J. Andre, *High Relaxivity for Monomeric Gd (DOTA)-Based MRI Contrast Agents, Thanks to Micellar Self-Organization*, Chem. Eur. J., 199, 5, 2977.

A. Accardo et al., *Physicochemical Properties of Mixed Micellar Aggregates Containing CCK Peptides and Gb Complexes Designed as Tumor Specific Contrast Agents in MRI*, J. Am. Chem. Soc., 2004, 126, 3097.
S. Aime et al., *High-Relativity Contrast Agents for Magnetic Resonance Imaging Based on Multisite Interactions between a β-Cyclodextrin Oligomer and Suitably Functionized $Gd^{III}$ Chelates*, Chem. Eur. J., 2001, 7, 5262.
D. Carr et al., *Intravenous Chelated Gadolinium as a Contrast Agent in NMR Imaging of Cerebral Tumours*, The Lancet, 1984, 3, 484.
W. Mulder et al., *A Liposomal System for Contrast-Enhaced Magnetic Resonance Imaging of Molecular Targets*, Bioconjugate Chem., 2004, 15, 799.
P. Caravan et al., *The Galolinuim (III)-Water Hydrogen Distance in MRI Contrast Agents*, Inorg. Chem., 2003, 42, 3972.
G. Vittadini et al., *B-19036, A Potential New Hepatobiliary Contrast Agent for MR Proton Imaging*, Invest. Radiol., 1988, 23, S246.
F. Uggeri et al., *Novel Contrast Agents for Magnetic Resonance Imaging*, Inorg. Chem., 1995, 34, 633.
P. Meier et al., *Substrate Specificity of Sinusoidal Bile Acid and Organic Anion Uptake Systems in Rat and Human Liver*, Hepatology, 1997, 26, 1667.
L. Pascola et al., *ABC Protein Transport of MRI Contrast Agents in Canalicular Rat Liver Plasma Vesicles and Yeast Vacuoles*, Biochem, Biophy. Res. Commun., 2001, 282, 60.
W. Schima et al., *MR Imaging of the Liver With Gb-BOPTA: Quantitative Analysis of T1-Weighted Images at Two Different Doses*, J.Magn. Reson. Imaging., 1999, 10, 80.
W. Davies et al., *Antiviral Activity of 1-Adamantanamine (Amantadine)*, Science, 1964, 144, 862.
J. Wang et al., *In Vitro Antitumor and Antimicrobial Activities of N-Substituents of Maleimide by Adamantane and Diamantane*, Chemotherapy 197, 43, 182.
D. Mannel et al., *Tumor Necrosis: Factors and Principles*, Immunol, Today, 1996, 17, 254.
A. Orzesko et al., *Synthesis and Anticancer Activity of 5-Phthaloylnucleosides*, Pharmazie, 2003, 58, 169.
W. Danysz et al., *Aminoadamantanes as NMDA Receptor Antagonists and Antiparkinsonian Agents-Preclinical Studies*, Neurosci, Biobehav. Rev., 1997, 21, 455.
V. Evidente et al., *A Pilot Study on the Motor Effects of Rimantadine in Parkinson's Disease*, Clin. Neuropharmacol., 1999, 22, 30.
R. Schwab et al., *Amantadine in the Treatment of Parkinson's Disease*, JAMA, 1969, 208, 1168.
K. Jain, *Evaluation of Memantine for Neuroprotection in Dementia*, Exp. Opin. Invest. Drugs, 2000, 9, 1397.

*Primary Examiner*—Michael G Hartley
*Assistant Examiner*—Jagadishwar R Samala
(74) *Attorney, Agent, or Firm*—Robert D. Katz; Cooper & Dunham LLP

(57) ABSTRACT

An adamantane functionalized magnetic resonance imaging (MRI) contrast agent has been synthesized, and shows high liver specificity, prolonged retention time in both the liver and kidneys, the highest relaxivity among clinical contrast agents, high water solubility, thermodynamic stability, signal intensity enhancement, hepatocellular uptake, and low osmolality and toxicity.

14 Claims, 9 Drawing Sheets

0 mins     8 mins     132 mins     180 mins 0 mins     8 mins     52 mins     180 mins 0 mins   8 mins   20 mins   32 mins   52 mins   132 min   160 mins   180 mins

OPTIMIZED RELAXIVITY AND SPECIFICITY HEPATOBILIARY MRI CONTRAST AGENT

CROSS-REFERENCE TO RELATED APPLICATION

This application claims the benefit of U.S. Provisional Patent Application No. 60/738,102, filed Nov. 21, 2005, the entire content of which is incorporated herein by reference.

BACKGROUND OF THE INVENTION

Magnetic resonance imaging is a noninvasive imaging modality in medical diagnosis with excellent soft tissue discrimination and high spatial resolution that outstrips conventional imaging techniques such as computed tomography (CT) and positron emission tomography (PET). With the unveiled human genome and advances in molecular biology, MRI has a far more wide ranging scope than it was originally envisaged. It penetrates into a variety of perspectives in the medical field such as the thornostic perspective, in the chemical engineering field, such as in the characterization of fluid flows and the visualization of structure-hydrodynamics relationships, and into pharmaceutical research, such as in the use in drug development that relates observation with the physiological mechanism. MRI constructs images by making use of the inherent natural abundance and the nature of the proton spins of the water molecules in human bodies. A superconducting magnet with homogenous magnetic field and radiofrequency pulses are the hardware, and the pharmaceutical contrast agents are the software. The use of contrast agents can improve the intrinsic poor sensitivity, especially in applications such as the targeting of specific cells or tissues at low concentration. Approximately 40% of MRI tests are contrast-enhanced annually, and this percentage is increasing, particularly with the urgent need for better molecular targeting contrast agents.

The biophysics of MRI contrast agents is the alternation of the relaxation rate, which is governed by paramagnetism. In addition to the proton density, two major mechanisms contribute to the degree of contrast enhancement: the longitudinal ($T_1$) and transverse relaxation ($T_2$). Relaxivity is a measure of the efficacy of the paramagnetic complexes in shortening the time for the relaxation processes at 1 mM concentration: a large value usually reflects a better in vivo performance. The small molecular gadolinium-based contrast agents are efficient $T_1$-agents that shorten the relaxation time and hence increase the relaxation rate. The observed relaxivity is composed of the innersphere relaxivity $R_{1p}^{IS}$, the outersphere relaxivity $R_{1p}^{OS}$, and the relaxation rate of the solvent in the absence of the paramagnetic complex, as shown in equation 1:

$$R_1^{obs} = R_{1p}^{IS} + R_{1p}^{OS} + R_1^W \qquad \text{Equation 1}$$

Various parameters define the effects of the contrast agents on the relaxation mechanisms, such as the electronic correlation time $\tau_v$, the reorientational correlation time $\tau_R$, the residence lifetime $\tau_m$, etc. These parameters are interdependent. A paramagnetic metal centre such as iron, manganese, and gadolinium, determines the electronic relaxation time; gadolinium is preferred and widely used because of its seven unpaired electrons and the symmetric S-state that provide a large magnetic moment and a slow electronic relaxation rate. The control of the image contrast mainly depends on the longitudinal innersphere relaxation, which is expressed by Solomon-Bloembergen equations as equation 2-5 (Solomon, Phys. Rev., 1955, 99, 559) (Bloembergen, J. Chem. Phys., 1957, 27, 572) (Solomon and Bloembergen, J. Chem. Phys., 1956, 25, 261).

$$\frac{1}{T_1} = R_{1p}^{IS} = \frac{[M]q}{55.6(T_{1M} + \tau_m)}, \qquad \text{Equation 2}$$

$$\frac{1}{T_{1M}} = \frac{1}{T_1^{DD}} + \frac{1}{T_1^{SC}}, \qquad \text{Equation 3}$$

$$\frac{1}{T_1^{DD}} = \frac{2}{15}\left[\frac{\gamma_I^2 g^2 \mu_B^2 S(S+1)}{r_{GdH}^6}\right]\left(\frac{\mu_0}{4\pi}\right)^2\left(\frac{7\tau_{c2}}{1+\omega_s^2\tau_{c2}^2} + \frac{3\tau_{c1}}{1+\omega_I^2\tau_{c1}^2}\right), \qquad \text{Equation 4}$$

$$\frac{1}{T_1^{SC}} = \frac{2S(S+1)}{3}\left(\frac{A}{\hbar}\right)^2\left(\frac{\tau_{e2}}{1+\omega_s^2\tau_{e2}^2}\right), \qquad \text{Equation 5}$$

wherein [M] is the molar concentration of the paramagnetic ions, q is the number of coordinated water molecules per Gd, $\tau_m$ is the residence lifetime of the bound innersphere water molecule, and $1/T_{1M}$ are the longitudinal proton relaxation rates. $\gamma_I$ is the nuclear gyromagnetic ratio ($\gamma(H)$=42.6 MHz/Tesla), S is 7/2 for gadolinium ions, g is the electron g-factor, $\mu_B$ is the Bohr magneton, $r_{GdH}$ is the electron spin-proton distance, $\omega_I$ and $\omega_s$ are the nuclear and electron Larmor frequencies respectively, and A/h is the hyperfine or scalar coupling constant between the electron of the paramagnetic centre and the proton of the coordinated water. The correlation times are related by equations 6 and 7:

$$\frac{1}{\tau_{c1}} = \frac{1}{\tau_R} + \frac{1}{T_{1e}} + \frac{1}{\tau_m}, \qquad \text{Equation 6}$$

$$\frac{1}{\tau_{e1}} = \frac{1}{T_{1e}} + \frac{1}{\tau_m}, \qquad \text{Equation 7}$$

wherein $\tau_R$ is the reorientational correlation time (or the rotational correlation time) and $T_{1e}$ is the longitudinal electron spin relaxation time of the metal ion.

The interplay of these parameters is shown in FIG. 1, and is complicated by the effect of magnetic field strength. The typical field strength of the clinical MRI scanners is 20-60 MHz (0.47-1.5 T). To present a clearer picture of the influencing parameters, the discussion of the observed longitudinal relaxation will be based on the 20 MHz field strength of clinical scanners. The optimization of the relaxivity can be achieved in various ways, the first of which is to increase the number of coordinated water q, which is directly proportional to the relaxivity as expressed by equation 1. Usually, q=2 is preferred for the nine coordinated gadolinium ion to optimize relaxivity and maintain a stable chelation. Recently, an acyclic ligand system was reported (Raymond et al., J. Med. Chem., 2005, ASPS Article) as having two innersphere coordinated water molecules, and was thermodynamically stable with relaxivity of 7.2-8.8 mM$^{-1}$s$^{-1}$. The second determinant that works together with q is the residence lifetime of coordinated water $\tau_m$. There are two distinctive situations as shown in equations 3 to 7: one is a fast water exchange ($T_{1M} \ll \tau_m$), in which the residence lifetime is the dominant factor, and another is a slow water exchange ($T_{1M} \gg \tau_m$), where the relaxivity is dependent on the proton exchange and rotational and electronic relaxation time.

An increase in the water exchange rate ($1/\tau_m$) increases the relaxivity and the optimal value of $\tau_m$ is 30 ns at 20 MHz. The major limitation of small molecular Gd-based clinical agents is the slow water exchange rate. A fast exchange rate is better associated with a slow rotational correlation time $\tau_R$ as the third influencing parameter in equation 6: that is, a slower tumbling rate of the molecule to enhance relaxivity. The formation of covalently or noncovalently bound macromolecules, such as dendrimers (Kobayashi et al., *Bioconjugate chem.*, 2003, 14, 388; Sato et al., *Magn. Reson. Med.*, 2001, 46, 1169 and U.S. Pat. App. Pub. No. 2004/0037777 A1), linear polymers (Aime et al., *Inorg. Chem.*, 2000, 39, 5747) or proteins (Doucet et al., *Invest Radio.*, 1990, 25, S53), can efficiently retard the rotational motion. Alternatives are micellar self-assembly (André et al., *Chem. Eur. J.*, 1999, 5, 2977; Accardo et al., *J. Am. Chem. Soc.*, 2004, 126, 3097; Anelli et al., *Chem. Eur. J.*, 2001, 7, 5262) and incorporated liposomes (Bydder et al., *Lancet*, 1984, 3, 484; Nicolay et al., *Bioconjugate Chem.*, 2004, 15, 799). However, the increase in relaxivity is less than expected due to internal flexibility, and the difficulty in obtaining a well-defined molecular dimension hampers further clinical application. Finally, a reduction in distance between the metal centre and the water protons $r_{GdH}$ increases the relaxivity, since relaxivity has a sixth-order dependence on the distance as expressed by equation 4. Estimation shows that a decrease of 0.2 Å leads to a 50% increase in the innersphere relaxivity (Raitsimring et al., *Inorg. Chem.*, 2003, 42, 3972). By assessing different potential molecular architectures, the contrast agent development is accentuated to small molecular Gd-based contrast agents for higher relaxivity and specificity.

The first generation of clinically used contrast agents is listed in Table 1. The two embodiments of the Gd chelates are acyclic diethylenetriaminepentaacetic acid (DTPA) and cyclic 1,4,7,10-tetra(carboxymethyl)-1,4,7,10-tetrazacyclododecane (DOTA), the structures of which are shown in FIG. 2. They possess acetate pendant arms that wrap around the metal centre to form a stable gadolinium complex and provide hydrophilicity. Free gadolinium ions are highly toxic (Gd(III) aqua ion has $LD_{50}$ of 0.1-0.2 mmol kg$^{-1}$ in rats) and have to be strongly chelated by organic ligands to form stable complexes before administration.

TABLE 1

| Chemical Name, Generic Name, Brand Name | Hydration Number (q) | Charge | Relaxivity (mM$^{-1}$ s$^{-1}$)* |
|---|---|---|---|
| Gd-DTPA, gadopentetate dimeglumine, Magnevist ™ | 1 | 2− | 4.69 |
| Gd-BMA, gadodiamide, Omniscan ™ | 1 | 2− | 4.39 |
| Gd-BMEA, gadoversetamide, OptiMARK ™ | 1 | 2− | 4.70 (40) |
| Gd-BOPTA, gadobenate dimeglumine, MultiHance ™ | 1 | 2− | 5.20 |
| Gd-DOTA, gadoterate meglumine, Dotarem ™ | 1 | 1− | 4.73 |
| Gd-HP-DO3A, gadoteridol, ProHance ™ | 1 | 0 | 3.70 (40) |
| Gd-DO3A-butrol, gadobutrol, Gadovist ™ | 1 | 0 | 3.60 (40) |

*The relaxivities listed are at 20 MHz and 25° C., except those with the temperature in parentheses.

The clinical agents are regarded as intravenous extracellular agents with one innersphere water molecule, and the relaxivities fall in a range of 3-4 mM$^{-1}$ s$^{-1}$, which is far from the theoretical maximum of 100 mM$^{-1}$ s$^{-1}$ [1]. They are distributed in the intravascular and interstitial space and are eliminated through the glomerular filtration, thus allowing the evaluation of physiological parameters. The bolus injection is adopted to increase the concentration to attain reasonably high signal intensity for these low relaxivity and non-specific agents. Although these agents are safe and are eliminated within 24 hours, high dosages of high osmolality agents may induce pain or increase the risk of in vivo dissociation, such as GD-DTPA with an osmolality of 1.96 osmol kg$^{-1}$ versus that of 0.29 osmol kg$^{-1}$ of body fluid. Their common disadvantages are poor efficiency (low relaxivity) and specificity (not tissue or organ targeting). Tissue-specific agents are in increasing demand for the detection of focal anomalies and evaluate tissue function for more accurate diagnosis. Research is undertaken to find a better contrast agent for the detection and characterization of focal liver pathology non-invasively, especially the hepatocellular carcinoma (HCC), thus notably reducing conspicuity in the diagnosis of hepatic diseases via the CT scan and biopsy.

A vast number of Gd-based contrast agents emerged following the use of Gd-DTPA in 0.5 M injections in early 1988. Polyaminocarboxylate ligands are widely included, and are composed of nitrogen and oxygen hard donor atoms, such as DTPA and DOTA, to securely chelate the gadolinium ion. Despite the introduction of liver-specific contrast agents such as the Mn-DPDP mangafodipir (the first small molecular agents) and SPIO ferumoxides (reticuloendothelial system specific agents) to the clinical realm, most agents are gadolinium based and have better safety profiles and well-controlled structures. The intravenous bolus injection of Gd-DTPA-BMEA or Gd-DTPA produces the transient enhancement of the liver and its vasculature in temporally distinct phases. In the phase III clinical trial reported in 1999, both agents showed improvement in lesion conspicuity, had good tolerance at the 0.1 mmol kg$^{-1}$ dose, and had a well-documented record of excellent safety. These two gadolinium contrast agents depend on the hepatic arterial flow and intravenous bolus injection, which is not a sound contrast enhancing effect in liver imaging. Hence, significant hepatocellular uptake has to be achieved for further improvement.

The recently approved hepatocyte specific agent in the second generation of contrast agents is Gd-BOPTA (MultiHance™). It is an acyclic contrast agent that is based on DTPA with a lipophilic benzyl group, and was first reported by Vittadini et al. in 1988 (Vittadini et al., *Invest. Radiol.* 1988, 23, 246) and its clinical trials were completed in 2000. This monoaqua complex adopts a distorted tricapped trigonal prism with three nitrogen atoms and five carboxylate oxygen atoms that occupy eight coordination sites (Uggeri et al., 1995, 34, 633). The relaxivity 5.2 mM$^{-1}$ s$^{-1}$ of Gd-BOPTA is the highest among the four acyclic contrast agents. It distributes throughout the extracellular space with moderate clearance, followed by the hepatic uptake. The hepatic uptake is around 3-5% of the injected dose, and it displays a leveling off in the signal intensity upon a concentration increase, possibly by the saturation in the biliary excretion. These properties are postulated to be caused by the increase in hydrophobicity in the presence of the lipophilic side arm or an increase in intracellular microviscosity within the hepatocyte, combining interactions with transport proteins such as glutathione-S-transferase and non-specific intereactions with other proteins. The advantage is the standard dose of 0.1 mmol kg$^{-1}$ can be reduced to 0.05 mmol kg$^{-1}$ (Bracco, S.P.A., Italy, MultiHance™). Even with a reduced dose Gd-BOPTA has greater lesion to liver contrast during the delayed phase (40-120 min) of the contrast enhancement than Gd-DTPA. The tumor signal intensity can be improved because either the tumors do not have hepatocyte or reticuloendothelial systems, or the functioning of intratumoral hepatocytes is hampered. This agent is taken up by hepatocytes and is partially excreted via the biliary system, or is taken up by the Kupffer cells of the reticuloendothelial system (RES). Another hepatobiliary agent under clinical trial is Gd-EOB-DTPA, which has a specific uptake via hepatocytes but not hepatoma cells. These advances demonstrate the importance of specific uptake to a better quality of MRI imaging.

The liver efficiently extracts a large variety of albumin-bound amphipathic compounds from sinusoidal blood plasma. The Kupffer endothelial cell constitutes the sinusoidal endothelium, which is a barrier between the blood and the hepatocytes that can hamper the passage of viral particles to the hepatocytes. Hepatocytes have multispecific uptake systems, namely the sinusoidal (basolateral) and canalicular transport pathways. These include two hepatocellular carrier proteins, the $Na^+$/taurocholate cotransporting polypeptides (NTCP) and the organic anion transporting polypeptides (OATP), which present at the basolateral plasma membrane of the hepatocyte (Meier et al., Hepatology, 1997, 26, 1667). As reported, the most probable carrier-mediated uptake pathway of hepatic contrast agents (Gd-BOTPA and Gd-EOB-DTPA) is through the OATP system and the possible biliary excretion pathways are excretion via ATP binding cassette (ABC) proteins, mainly by the multidrug resistance-associated protein 2 (mrp2) (Tiribelli et al., Biochemical and Biophysical Research Communications, 2001, 282, 60). The hydrophobic moieties enhance the uptake by the hepatocyte.

Acyclic ligands, such as Gd-DTPA and Gd-BOPTA, are subjected to kinetic lability. This endeavors to the investigation of cyclic ligands, such as Gd-DOTA, having selective and efficient complexation with their size-shape complementarity and preorganization. However, the formation of macrocycles is kinetically unfavourable. Much effort was devoted to the synthetic procedures for higher yield by either boosting the reactivity of the participating reagents and to suppress the linear oligomerization of reactants. In the regard of osmolality, neutral macrocyclic ligands are preferred. Under these two concerns, one class of macrocycle DTPA-bis(amide), which involves the cyclolization of DTPA dianhydride and diamine; yielding a convenient one-step and high yield preparation, attracts attentions. The three carboxylic arms encapsulate the gadolinium ion resulting in neutral complexes with the thermodynamic log $K_{GdL}$ of 15-19 (Meier et al., Hepatology 1997, 26, 1667).

Improvements in MRI contrast agents have been carried out in connection with: (1) relaxivity (e.g., >4 $mM^{-1}s^{-1}$) and in vivo stability, (2) specificity towards tissues or organs, (3) stabilities, and (4) percentage uptake by the hepatocytes (e.g., >5%).

SUMMARY OF THE INVENTION

The invention provides the high yield synthetic procedures for a gadolinium (III) adamantane-1-carboxylic acid 4,7,10-tris(carboxylmethyl)-2,12-dioxo-1,4,7,10,13-pentaazacyclohexadecylester Gd-DTPA-PNAD (GdL) that is a DTPA-bis(amide) macrocycle with a rigid hydrophobic adamantane functional group. The $^1H$ NMRD profiles of GdL show a relaxivity of 5.96 $mM^{-1} s^{-1}$ with one innersphere water molecule, which is the highest among the clinical Gd-based contrast agents at 20 MHz under physiological pH ranges. The residence lifetime of the bound water molecule $\tau_m$ from the variable-temperature $^{17}O$ NMR represents a slow water exchange rate. Both the temperature and pH dependent longitudinal relaxivity show a favourable relaxivity and no significant dissociation under a wide pH window, especially in the basic extreme. The most crucial finding is the high specificity towards the liver in the in vivo study using the rat model. The hepatic and renal intensity enhancements at the standard dosage of 0.1 mmol $kg^{-1}$ are 95% and 86% respectively, much higher than the 55% for hepatobiliary agent Gd-BOPTA (Schima et al., J. Magn. Res. Imaging 1999, 10, 80).

The maximum intensity enhancement is found at 4 min post injection and lasts for more than 3 hours. In addition, the renal intensity has also been prolonged. The common problem of fast excretion of the small molecular clinical agents has been overcome. The non-tumorigenic immortalized liver cell (MIHA) uptake experiments prove that GdL is an intracellular agent with a relatively 74% increase in the hepatic uptake as compared with Gd-BOPTA. This is useful in both medical research, like intracellular studies; and diagnosis, like in situ tracing of the disease-related molecules. GdL adopts a dose-dependent uptake, but that dependence is not significant in the case of Gd-BOPTA. Furthermore, the toxicity of the agent against MIHA cells has been evaluated by MTT assay and the percentage of viability was well above 90% throughout the course of the experiment under a concentration range of 0.08-10 mM and at different incubation time. In summary, GdL is a better hepatobiliary agent with high efficacy in hepatic intensity enhancement and retention time. The increase in hepatic uptake and the low toxicity make the agent a promising and potential candidate for future liver-specific MRI contrast agents.

The present invention provides a magnetic resonance imaging (MRI) contrast agent (CA), which comprises a pendant adamantane compound and metal chelator, wherein the adamantane compound is covalently bonded with a metal chelator that contains a paramagnetic ion. In one embodiment, the compound can have the following structure:

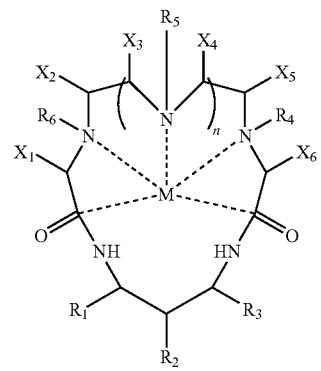

wherein M is a paramagnetic metal ion; only one of $R_1$-$R_3$ comprises an adamantane compound, and $R_4$-$R_6$ are the chelating groups —$CH_2COO^-$, —$CH_2COO$—, —$CH_2CONH$—, —$CH_2COC$—, —$CH_2OH$, —$CH_2P(O)$(OEt)(OH), —$CH_2P(O)(OEt)(Ph)$, —$CH_2P(O)(OEt)\{CH_2N(CH_2Ph)_2\}$ or —$CH_2O$—; $X_1$-$X_6$ each comprise hydrogen, alkyl, aryl, alcohol, amine, amido, nitro, ether, ester, ketone, imino, aldehyde, alkoxy, carbonyl, halogen, sulfur containing moieties, phosphorous containing moieties, silicon containing moieties, or other blocking moieties, or together with an adjacent X group are alkyl or aryl groups; n=0-3; monosubstituted or trisubstituted adamantane modifications comprise hydrogen, alkyl, aryl, alcohol, amine, nitro, ether, ester, ketone, imino, aldehyde, alkoxy, carbonyl, halogen, sulfur containing moieties, phosphorous containing moieties, silicon containing moieties; and either one water molecules are directly coordinated with the paramagnetic metal ion.

The compound can be an MRI CA and the paramagnetic metal ion is chromium(III), manganese(II), iron(II), iron(III), cobalt(II), nickel(II), copper(II), zinc(II), praseodymium (III), neodymium(III), samarium(III), europium(III), gadolinium(III), terbium(III), dysprosium(III), holmium(III), erbium(III), thulium(III), ytterbium(III), or a combination thereof. For example, the paramagnetic metal ion can be gadolinium(III). The compound can be an MRI CA and the macrocyclic chelator can be 4,7,10-tris(carboxylmethyl)-2, 12-dioxo-1,4,7,10,13-pentaazacyclohexadecylester.

The adamantane compound can be connected to a metal chelator with alkyl, allyl, alkyne, aryl, amide, ester, ether, ketone, imino group, phosphorous containing moieties, sulfur containing moieties, silicon containing moieties, ethylene glycol, polyethylene glycol, peptide, or polypeptide.

In another embodiment, the MRI contrast agent can have the following structure:

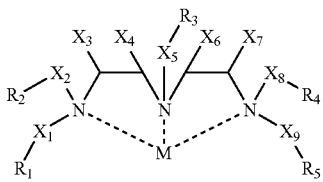

wherein, M is a paramagnetic metal ion; one of $R_1X_1$, $R_2X_2$, $R_3X_5$, $R_4X_8$, $R_5X_9$ form an adamantane compound, and the remaining are the chelating groups $CH_2COO^-$, $—CH_2COO—$, $—CH_2CONH—$, $—CH_2COC—$, $—CH_2OH$, $—CH_2P(O)(OEt)(OH)$, $—CH_2P(O)(OEt)(Ph)$, $—CH_2P(O)(OEt)\{CH_2N(CH_2Ph)_2\}$ or $—CH_2O—$; $X_1$-$X_9$ each comprise hydrogen, alkyl, aryl, alcohol, amine, amido, nitro, ether, ester, ketone, imino, aldehyde, alkoxy, carbonyl, halogen, sulfur containing moieties, phosphorous containing moieties, silicon containing moieties, or other blocking moieties, or together with an adjacent X group are an alkyl or aryl groups; monosubstituted or trisubstituted adamantane modifications comprise hydrogen, alkyl, aryl, alcohol, amine, nitro, ether, ester, ketone, imino, aldehyde, alkoxy, carbonyl, halogen, sulfur containing moieties, phosphorous containing moieties, or silicon containing moieties; and either one or two water molecules are directly coordinated with the paramagnetic metal ion.

In an embodiment, the compound can be an MRI CA and the paramagnetic metal ion can be chromium(III), manganese (II), iron(II), iron(III), cobalt(II), nickel(II), copper(II), zinc (II), praseodymium(III), neodymium(III), samarium(III), europium(III), gadolinium(III), terbium(III), dysprosium (III), holmium(III), erbium(III), thulium(III), ytterbium(III), or a combination thereof.

In another embodiment, the adamantane compound can be connected to a metal chelator with alkyl, allyl, alkyne, aryl, ester, ether, ketone, imino group, phosphorous containing moieties, sulfur containing moieties, silicon containing moieties, ethylene glycol, polyethylene glycol, peptide, or polypeptide.

According to another aspect of the present invention, a method is provided for liver imaging, which comprises the administration of the MRI contrast agent of claim 2 to a subject, permitting the agent to accumulate at a site of liver parenchyma in the liver for which an image is desired, and performance of an MRI scan of the site and generating an image therefrom. In one embodiment of the method, the MRI contrast agent shows significant organ/tissue specificity to the liver. The maximum liver intensity enhancement is reached in a few minutes after the administration of the contrast agent.

According to a further aspect of the present invention, a method is provided for kidney imaging, which comprises the administration of the MRI contrast agent of claim 2 to a subject from which an image is desired; and performance of an MRI scan of the site and generating an image therefrom. In one embodiment of the method, the MRI contrast agent shows significant organ/tissue specificity to the kidneys. The maximum kidney intensity enhancement is reached a few minutes after the administration of the contrast agent.

DETAILED DESCRIPTION OF THE INVENTION

Figure 1:
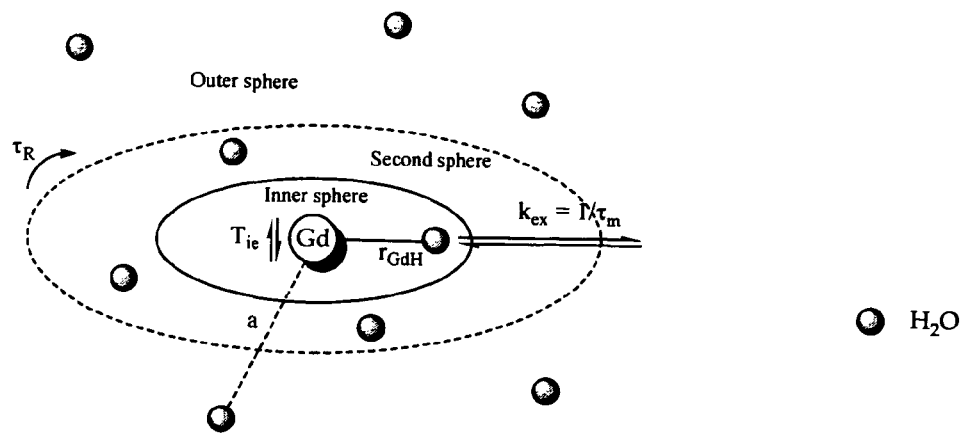
FIG. 1 shows a Gd(III) complex with one innersphere water molecule. $\tau_R$ and $\tau_m$ are the reorientational correlation time and the residence lifetime respectively; $T_{ie}$ with i=1, 2 is the electronic relaxation time; $r_{GdH}$ is the distance between the metal ion and the innersphere water proton; and a is the average distance with the bulk water.
Figure 2:
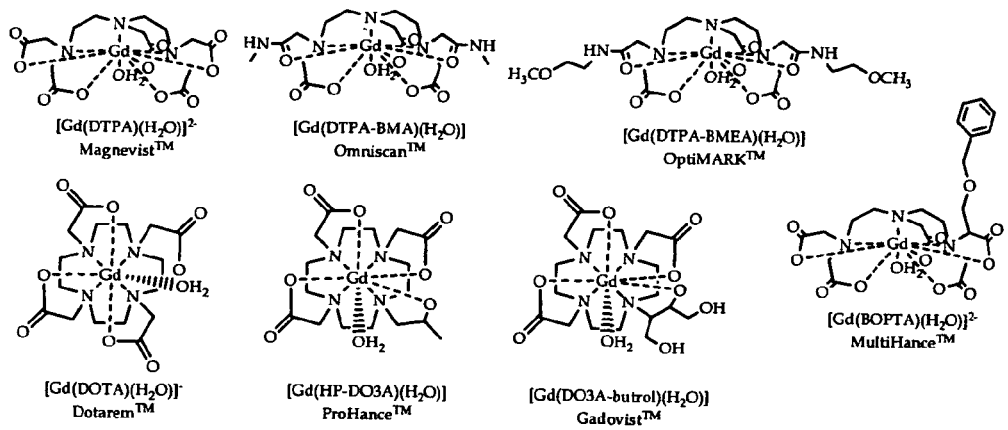
FIG. 2 shows the structures of clinically approved gadolinium based MRI contrast agents.

The specific abbreviations and terms are listed as follows to facilitate the review of the various embodiments of the invention.

Abbreviations
MRI—magnetic resonance imaging
CAs—contrast agents
DTPA—diethylenetriaminepentaacetic acid
DOTA—1,4,7,10-tetra(carboxymethyl)-1,4,7,10-tetraazacyclododecane
DO3A—1,4,7-tris-(acetic acid)-1,4,7,10-tetraazacyclododecane
NMRD—nuclear magnetic resonance dispersion
SB—Solomon-Bloembergen
BM—Bloembergen-Morgan
ZFS—zero-field splitting
BOPTA—4-carboxy-5,8,11-tris(caroxymethyl)-1-phenyl-2-oxa-5,8,11-triazatridecan 13-oic acid
EOB-DTPA—(S)-N-[2-[bis(carboxymethyl)amino]-3-(4-ethoxyphenyl)propyl]-N-[2-[bis(carboxymethyl)amino]-ethyl]glycine
DTPA-bis(amide)—2,12-dioxo-1,4,7,10,13-pentaaza-4,7,10-cyclohexadecanetriacetic
MIHA—non-tumorigenic immortalized liver cell line Terms Unless otherwise explained, all technical and scientific terms used herein have the same meaning as commonly understood by one of ordinary skill in the art to which this invention belongs. The singular terms "a", "an", and "the" include plural referents unless the context clearly indicates otherwise. Similarly, the word "or" is intended to include "and" unless the context clearly indicates otherwise. The term "comprises" means "includes".

The invention is a novel gadolinium-based MRI contrast agent that is derived from the DTPA-bis(amide) macrocycle functionalized with hydrophobic adamantane that shows a high relaxivity and liver specificity, which enables favourable physiochemical and pharmacokinetics properties such as high water solubility, stability, no hint of dissociation after dosing, long retention time, complete excretion, low toxicity, and low osmolality.

The diamondoid framework of adamantane has numerous applications in medicinal chemistry, especially the membrane permeability and conformational constraint for efficient ion transport in lipid bilayers. A well-know provenience is the 1-aminoadamantane (amantidine) that is used for prophylaxis and the treatment of type A influenza (Hoffmann et al., *Science* (Washington D.C.), 1964, 144, 282); others show antiviral, antibacterial, or anticancer activities (Chern et al., *Chemotherapy*, 1997, 43, 182; Claus et al., *Immunol. Today*, 1996, 17, 254; Kamińska et al., *Pharmazie*, 2003, 58). With modifications, adamantadine and rimantidine become promising for treatment of Parkinson's disease (Quack et al., *Neurosci. Biobehav. Rev.*, 1997, 21, 455; Hardy et al., *Clin. Neuropharmacol.*, 1999, 22, 30; Young et al., *J. Am. Med. Associ.*, 1969, 208, 1168) or Alzheimer's disease (Jain et al., *Expert. Opin. Invest Drugs*, 2000, 9, 1397), stimulating TNF-α production. Adamantane also shows affinity towards the gamma-aminobutyric acid (GABA) receptor or glutamate receptors (GluR). Its rigid hydrophobic cage and low molecular weight enhance lipophilicity and biological availability, enabling the differential cell membrane affinity, particularly on the basis of different distribution of the interacting sites. This is essential for the carrier-mediated hepatocyte uptake. Furthermore, the adamantane has potential to form inclusion complexes with cyclodextrins in a host-guest nature through Van der Waals interaction, hydrophobic interaction, hydrogen bonding, or steric effects. The inclusion complexes formed are both enthalpically and entropically favourable and are interested because of the magnification of the relaxivity by retarding the tumbling rate $\tau_R$. Different degrees of relaxivity enhancements are found in the inclusion complexes formed by gadolinium DTPA and DOTA derivatives and poly-β-cyclodextrin. The enhancement found were at most six times the Gd complex itself (Evidente et al., *Clin. Neuropharmacol.* 1999, 22, 30). The unlimited possibilities of adamantane may open new areas in drug development and in studying low concentration receptors.

Figure 3:
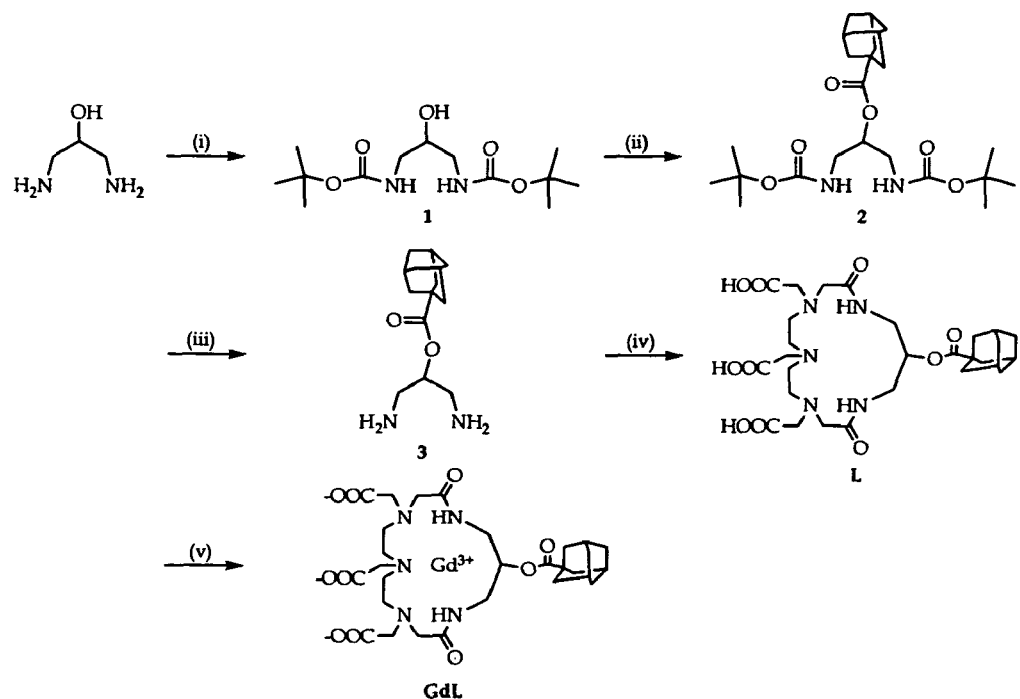
FIG. 3 shows the synthetic procedure of GdL preparation with the reagents and conditions: (i) di-tert-butyldicarbonate, MeCN, r.t., 1 h, 90%; (ii) adamantane-1-carbonyl chloride, $CH_2Cl_2$, Py, 60° C., 12 h, 60%; (iii) trifluoroacetic acid, $CH_2Cl_2$, $N_2$, 10 h, 80%; (iv) DTPA dianhydride, DMF, r.t., 24 h, 65%; (v) $Gd_2(CO_3)_3$, $H_2O$, 65° C., 24 h, 90%.
Figure 4:
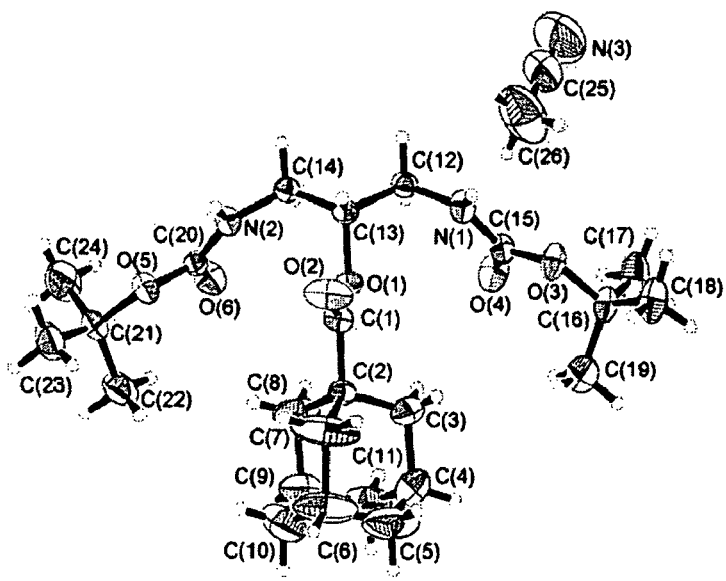
FIG. 4 shows an ORTEPII (Johnson, 1976) drawing of the molecular structure of (3), showing 50% probability displacement ellipsoids and the crystallographic labeling scheme.

The ligand was prepared according to the high yield synthetic procedures and reaction conditions that are described in FIG. 3. First, the primary amines of 1,3-diaminopropanol were protected with the addition of 2.5 equivalent of the tert-butoxycarbonyl (BOC) groups in $CH_3CN$. Second, the hydroxyl group reacted with the active carbonyl chloride functionized adamantane in $CH_2Cl_2$/Py (structure shows in FIG. 4). Finally, the deprotection in TFA/$CH_2Cl_2$ frees the amines for the condensation with the freshly prepared DTPA dianhydride under high dilution. Although the yield of the grafting of adamantane was slightly lower at about 60%, the BOC protection and deprotection were high yield procedures with an average of 85% yield. The overall yield is high with this effective diamine modification. The complexation with $Gd_2(CO_3)_3$ in water was used for the formation of the complex GdL.

Relaxivity is used to describe the efficiency of a paramagnetic substance in increasing the water longitudinal relaxation rate. NMRD profiling is a direct method of measuring the proton relaxivity, and in principle it is sensitive to all of the parameters that influence relaxivity. It is the nuclear relaxation rate ($1/T_1$) as a function of the Larmor frequency or the magnetic field, and describes the excess longitudinal proton relaxation that is caused by the presence of contrast agents as a function of the magnetic field using a field-cycling technique. The NMRD profile can probe the relaxivity mechanisms and understand how changes in the chemical structure of the complex interfere with them. The change in experimental parameters such as temperature and pressure influences the physical or chemical state of the sample, but the variation of the magnetic field has no influence on the chemistry of the sample. Thus, NMRD is a useful technique in the understanding of the numerous physiochemical parameters that determine the field dependence of proton relaxivities. The innersphere, outersphere, and second sphere contribute to the overall relaxivity and are influenced by numerous parameters, which are too complex to be well-defined by a single NMRD study; usually, reference to independent $^{17}O$ NMR relaxation rates and chemical shift is made. By the equations 2-7, several parameters that are related to the outersphere, and innersphere relaxation, such as the hydration number q, the $\tau_m$, $\tau_R$, $\tau_v$, $\Delta^2$, and $r_{GdH}$, can be estimated.

Figure 5:
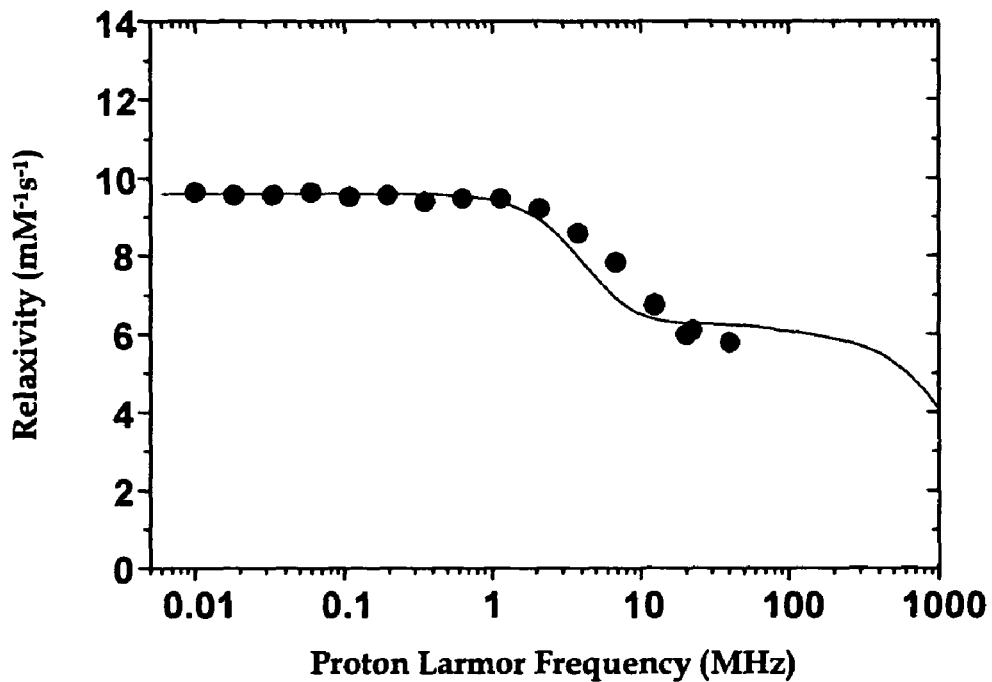
FIG. 5 shows the NMRD profile of GdL at 25° C. and pH 7.2 ($\tau_m$=0.93 μs, a=3.8 Å and D=2.24E-5 $cm^2s^{-1}$).

The NMRD profile of GdL shows a relaxivity of 5.96 $mM^{-1} s^{-1}$ at 20 MHz, 7.2 pH and 25° C. in FIG. 5, which is 26% higher than the cyclic clinical contrast agent Gd-DOTA at 4.73 $mM^{-1}s^{-1}$, and 15% higher than the acyclic hepatobiliary contrast agent Gd-BOPTA at 5.20 $mM^{-1}s^{-1}$ under the same condition. As shown in FIGS. 5-8, all complexes have one innersphere water molecule. At low field, the electronic relaxation dominates the dipole-dipole correlation time for innersphere relaxivity and results in the first dispersion at around a 34 MHz proton Larmor frequency, while at high field, rotation relaxation dominates and the dispersion is at around 30 MHz. The higher relaxivity as compared to the clinical agents is postulated to the longer reorientational correlation time $\tau_R$ and the shorter $r_{GdH}$. Relaxivity has a dependence on the $\tau_R$ at 20 MHz, which is determined by the molecular dimension. As GdL is a larger macrocycle and has a higher molecular weight of 766 Da, the tumbling rate of the innersphere water molecule is significantly slowed down, promoting the relaxivity. In addition, the $r_{GdH}$ has a sixth-order dependence on the relaxation; with a 0.14 Å shorter distance, relaxivity is greatly improved.

formation constants are $\Sigma$ $pK_a$=17.36 and $\Sigma$ log $K_{GdLH_n}$=19.76 respectively. The first protonation $K_1$ takes place on the central amine nitrogen. When the second protonation occurs, a redistribution of protons between amine nitrogen atoms is observed. The log $K_2$ and $K_3$ values come from the protonation of the carboxylates that are adjacent to the first protonated amine nitrogen. For the formation constants, the amide carbonyl oxygens of this medium cavity participate in the metal chelation, which results in a more stable complex.

In vivo investigation using the rat model is effective in studying the pharmacokinetics of MRI contrast agents such as biodistribution and excretion. The low molecular weight gadolinium agents (such as Gd-DTPA and Gd-DOTA) have extracellular distributions and do not pass through the plasma

TABLE 2

Fitting parameters obtained from the analysis of the NMRD profile and $^{17}$O transverse relaxivity study according to a preferred embodiment of the present invention

| Complex | Molecular Weight (Da) | $R_{1p}$* (mM$^{-1}$s$^{-1}$) | $\Delta^2$ (E19 s$^{-1}$) | $\tau_v$ (ps) | $\tau_r$ (ps) | $\tau_m$ (ns) | $r_{GdH}$ (Å) |
|---|---|---|---|---|---|---|---|
| GdL | 766 | 5.96 | 4.0 | 18.9 | 135 | 930 | 2.98 |
| Gd-DOTA | 557 | 4.73 | 1.3 | 7.7 | 73 | 300 | 3.10 |
| Gd-DTPA | 545 | 4.69 | 4.2 | 20 | 73 | 250 | 3.10 |
| Gd-BOPTA | 665 | 5.20 | 4.2 | 26 | 88 | 200 | 2.96 |

*Relaxivities listed are at 20 MHz and 25° C.

Figure 6:
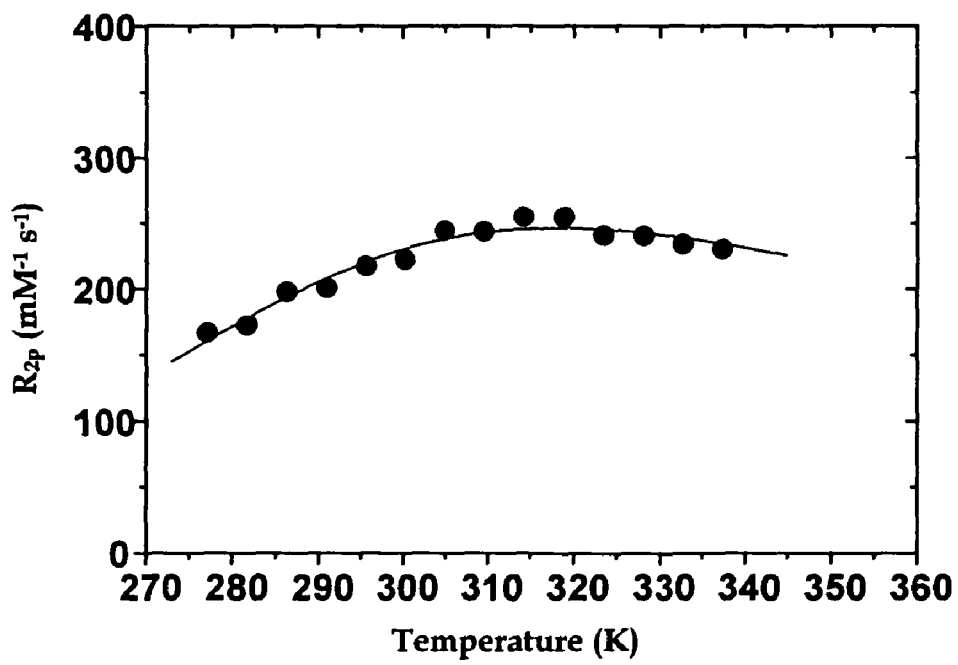
FIG. 6 shows the temperature dependence of $^{17}O$ NMR transverse relaxation rate of GdL.
Figure 7:
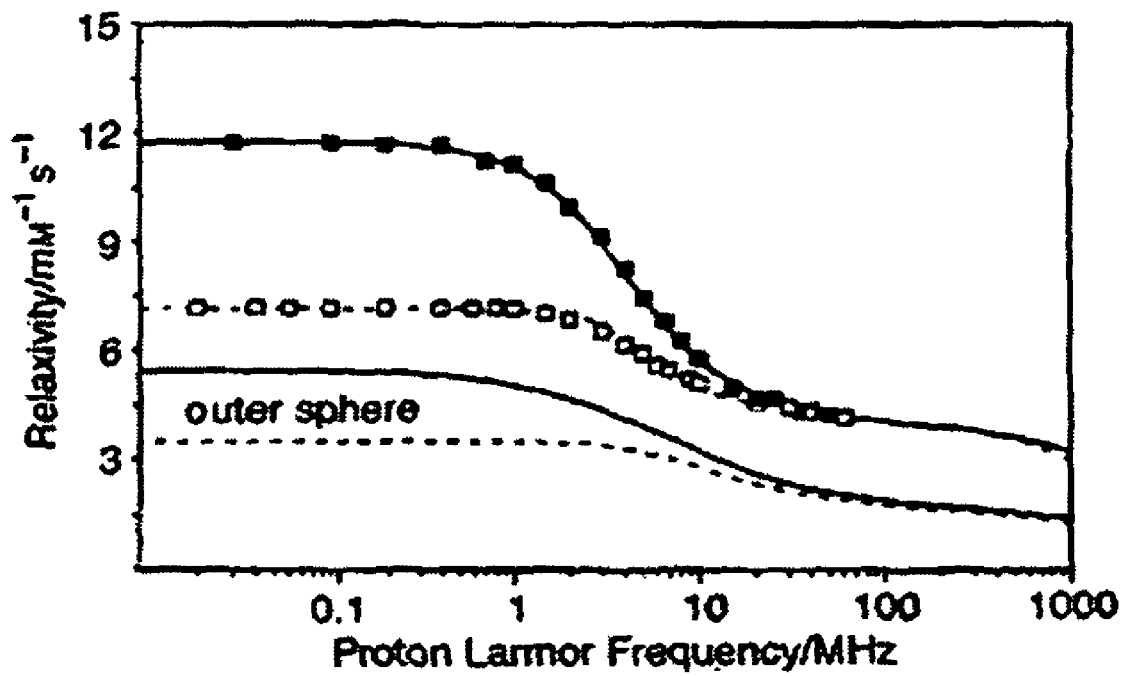
FIG. 7 shows the NMRD profiles of Gd-DOTA (in empty square) and Gd-BOPTA (in filled square) at 25° C. and pH 7.4. The lower curves are the outersphere contributions.
Figure 8:
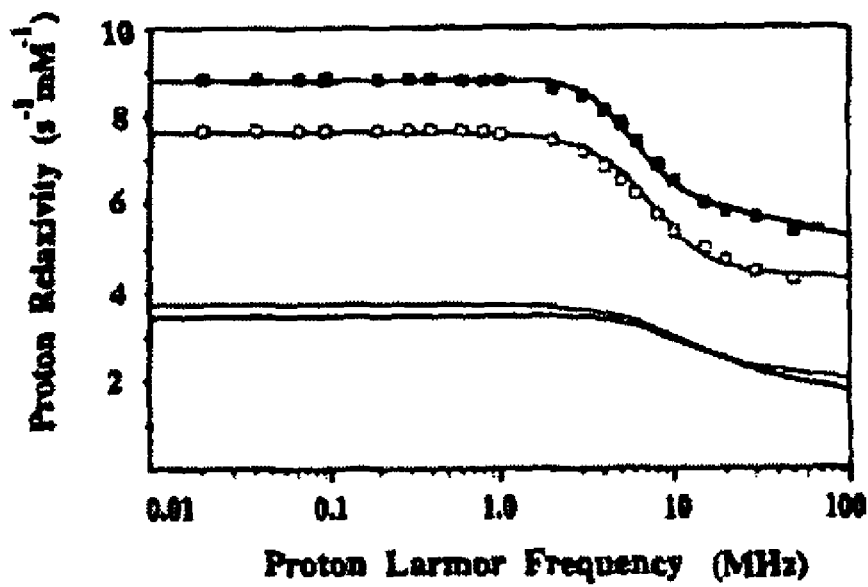
FIG. 8 shows the NMRD profiles of the commercial contrast agents, Gd-DTPA (in filled square) and Gd-DOTA (in empty square) at 25° C. and pH 7.4. The lower curves are the outersphere contributions.

Further investigation into the transverse relaxivity changes against temperature as shown in FIG. 6 was performed to determine the exchange rate. The maximum appears at a lower temperature, which implies a faster water exchange rate. The water exchange rates of the discussed ligands are in the order of Gd-BOPTA ($k_{ex}$=5.0×10$^6$)>Gd-DTPA ($k_{ex}$=4.0×10$^6$)>Gd-DOTA ($k_{ex}$=3.3×10$^6$)>GdL ($k_{ex}$=1.1×10$^6$). As anionic complexes promote water exchange, the first three complexes are anionic species with faster water exchange rates. GdL is neutral with a lower exchange rate, but with a lower osmolality, and importantly, the highest relaxivity.

Figure 9:
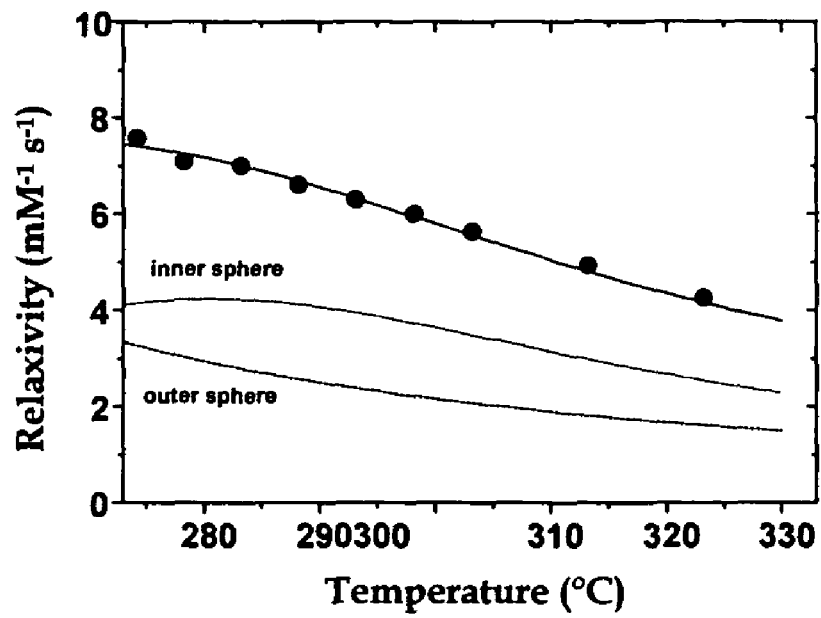
FIG. 9 shows the temperature dependence of the longitudinal relaxivity of GdL.
Figure 10:
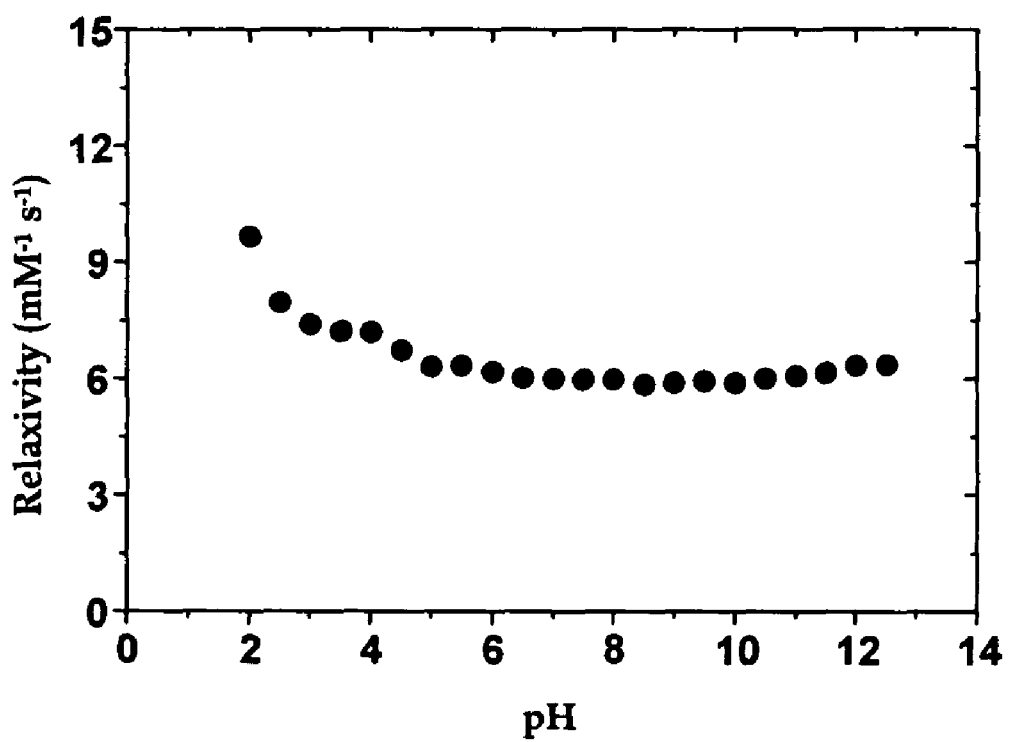
FIG. 10 shows the pH dependence of the longitudinal relaxivity of GdL.
Figure 11:
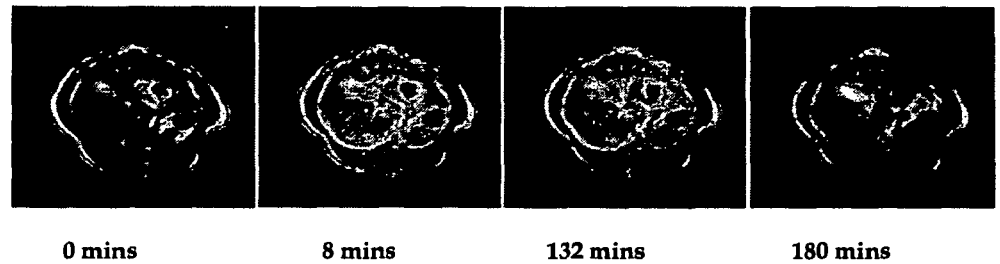
FIG. 11 shows the MR images of the transverse section of the liver before (control) and after the administration of GdL with standard dosage (0.1 mmol $kg^{-1}$).
Figure 12:
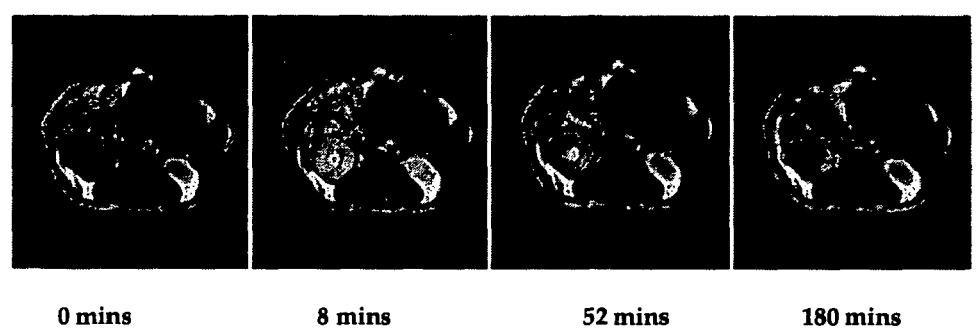
FIG. 12 shows the MR images of the transverse section (upper part) and the longitudinal section (lower part) of the kidneys before (control) and after the administration of GdL with standard dosage (0.1 mmol $kg^{-1}$).
Figure 12:
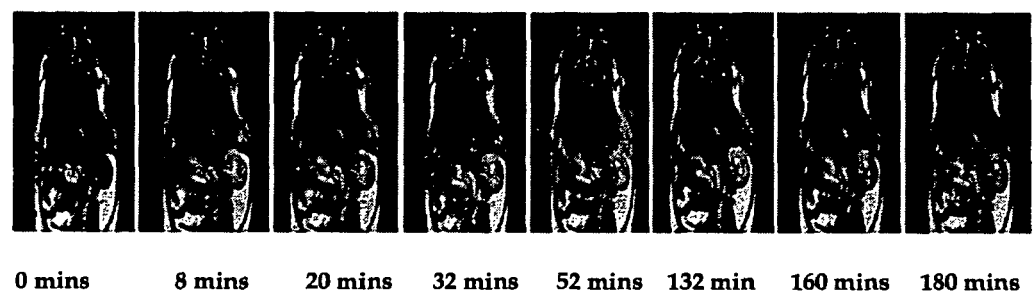
Figure 13:
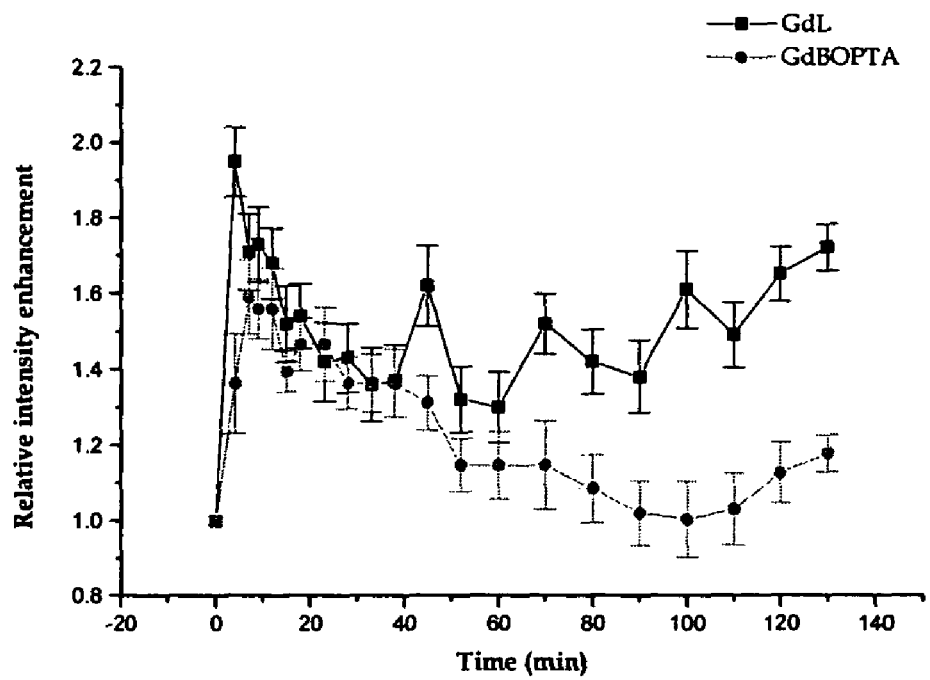
FIG. 13 shows the time dependence of the $T_1$-weighted hepatic relative intensity enhancements that are induced by the administration of GdL and GdBOPTA at standard dosages.
Figure 14:
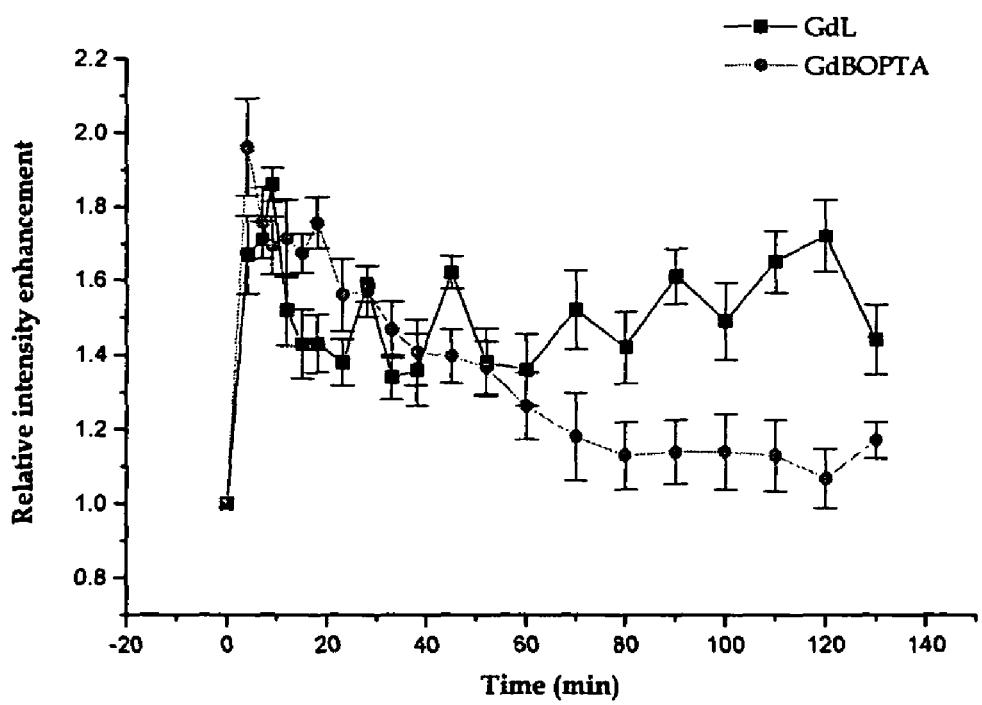
FIG. 14 shows the time dependence of the $T_1$-weighted renal cortex relative intensity enhancements that are induced by the administration of GdL and GdBOPTA at standard dosages.

The temperature and pH dependence of the longitudinal relaxivity were measured to study the tolerance of the complex under different physiological conditions (see FIGS. 9-10). At the low temperature under the slow exchange rate ($\tau_m$>>$T_{1M}$) a relatively longer $\tau_m$ is insignificant. The innersphere quenching is not severed and is not dominated by the outersphere mechanism at 273-278 K. Beyond 278 K the innersphere contribution increases up to 288 K. This is the $\tau_m \approx T_{1M}$ region, where the onset of the innersphere and the slow water exchange is not interfered with. From 288 K to 330 K, there is a gradual drop in the relaxivity due to the increase in D and $T_{1M}$ which causes both the innersphere and outersphere relaxivities to fall under the fast exchange condition ($\tau_m$<<$T_{1M}$). The relaxivity is 4.93 mM$^{-1}$s$^{-1}$ at physiological temperature. The acid-catalyzed proton exchange is mild and the base-catalyzed proton exchange is insignificant, which indicates a constant relaxivity over a wide pH range from 2.5 to 12.5 pH. The structural arrangement around the metal centre is not severely distorted, which allows a high stability against different pH.

Thermodynamic stability is an essential criterion for the in vivo applications, due to the chemotoxicity that arises from the free metal ions or the free ligands. It is determined by potentiometry and a high thermodynamic stability indicates the less probable of the dissociation. The protonation and membrane and the blood brain barrier, and mainly excreted via the renal pathway. Hence, they are regarded as extracellular fluid space agents. Gd-BOPTA is a hepatobiliary agent with a 3-5% hepatocellular uptake in humans and 38.6% hepatocellular uptake in rats. It displays a leveling off in the signal intensity upon a concentration increase, possibly through saturation in the biliary excretion. Other pharmacokinetic properties closely resemble those in humans, therefore in vivo studies based on small animal models are necessary and powerful tools to provide evidence of the stability, safety, in vivo intensity enhancement, possible targeting sites, retention time and distribution under the physiological environment.

A series of $T_1$-weighted images were obtained at the transverse section at 4-min intervals up to 180 min after the administration of GdL at the standard dosage of 0.1 mmol kg$^{-1}$. The longitudinal and transverse section images of the abdomen were scanned, focusing on the liver and the kidneys. The intensity enhancements of the two organs were measured as a function of time. The maximum signal intensity of the liver and kidneys were 95% and 86% respectively (see FIGS. 11-14). These maxima were reached immediately at 4 min after administration for the liver, and at 12 min for the kidneys. The efficacy of liver imaging is exceptionally good. First, the intensity maximum is reached immediately after administration. Second, the IE is high. After a gradual drop, the IE remains at a plateau region for at least 2 hours. The half-life of the liver is 104 min and of the kidneys is 89 min. These long half-lives improve the clinical practice by using one dose for a complete scan, i.e. avoiding the bolus injection or multiple injections.

Figure 15:
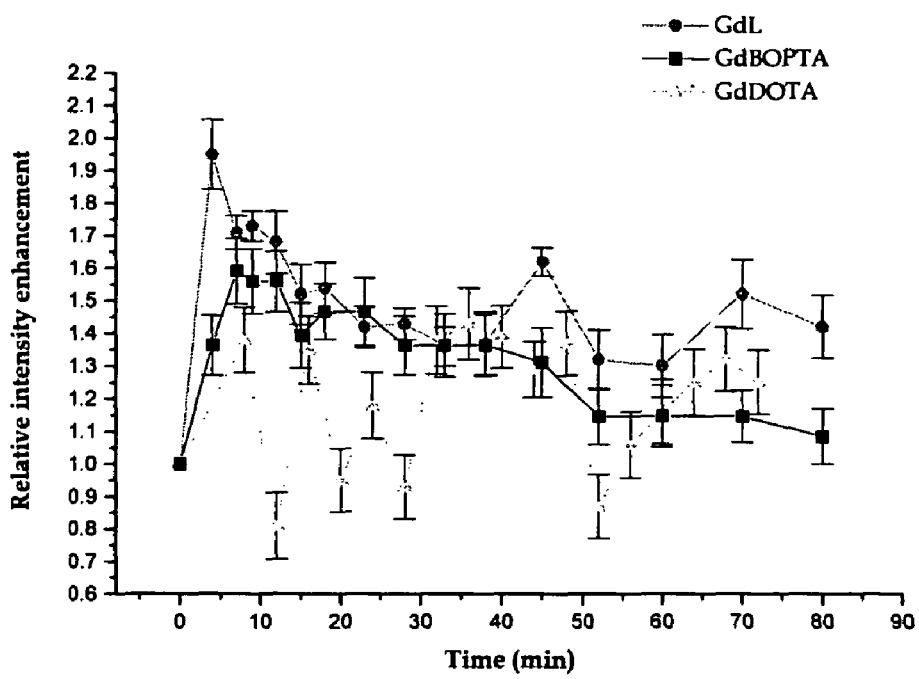
FIG. 15 shows the time dependence of the $T_1$-weighted hepatic relative intensity enhancements that are induced by the administration of GdL, GdBOPTA, and GdDOTA at standard dosages.

With respect to the liver specificity, the hepatobiliary agent Gd-BOPTA and a typical cyclic contrast agent Gd-DOTA were studied under the same conditions as GdL. The IE of GdL showed a 45% increase versus Gd-DOTA and a 23% increase versus Gd-BOPTA in the first 60 min (as shown in FIG. 15). In the delay phase from 60-180 min, the IE remains at a level of 1.4 times higher than that of Gd-BOPTA. The IE remains high above 50 and 40 for liver and kidneys respectively, and lasts for at least 2.5 h. No side effects were observed during the 12 h following the administration. GdL is a better hepatobiliary agent than the clinical agents.

In rats, the anatomic absence of the gallbladder impairs the visualization of enhanced bile and the bile ducts; moreover, the blood circulation is faster, which leads to a faster distribution and faster elimination half-lives than in humans. This was demonstrated by a study of Gd-EOB-DTPA, where there was a 50% uptake of the injected dose in humans while in rats there the uptake was 70%. These discrepancies can be explained by the much lower organic anion transport capacity that has been reported in humans than in rat hepatocytes, due to the difference between human OATP and the rate oatp1 in both the structural and functional levels. The efficacy and correlation between rats and human may be verified by in vitro hepatocellular uptake studies. Cell studies, especially physiological, pharmacological, and toxicological studies, are beneficial for the understanding of in vivo drug absorption and may be extremely valuable for the further development of contrast agents.

Figure 16:
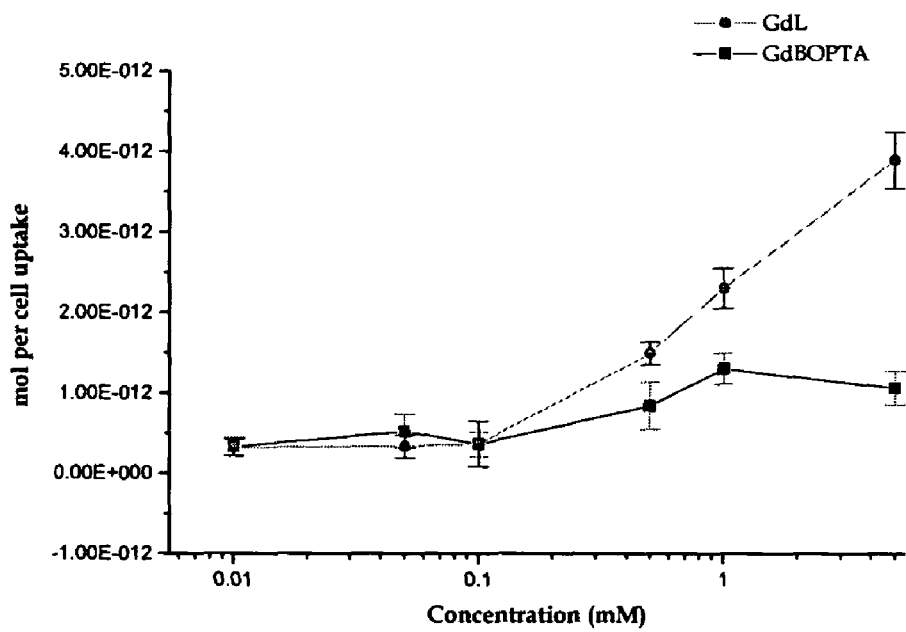
FIG. 16 shows the dependence hepatocellular uptake of GdL and GdBOPTA at different incubation concentrations using MIHA.

The non-tumorigenic immortalized liver cell line (MIHA) was grown and incubated in different concentrations of GdL and Gd-BOPTA. The mole of gadolinium uptake per cell under different concentrations of GdL incubation is presented as a function of concentration in FIG. 16. A significantly larger uptake is found in GdL relative to Gd-BOPTA—the clinical hepatobiliary contrast agent. The average increase is $7.2 \times 10^{-13}$ mole of Gd per cell (about 1.97 times more than Gd-BOPTA) and the maximum uptake is $3.1 \times 10^{-12}$ mol of Gd per cell at 5 mM. There was no gadolinium ion found in the control experiments in the absence of GdL. The uptake varied slightly at the incubation concentration of less than 0.5 mM and linearly when the concentration increases from 0.5 to 5 mM. Gd-BOPTA is an intracellular agent after 45 min of intravenous injection in humans; therefore, over 95% percentage of contrast agents is excreted. A larger quantity hepatocellular uptake than Gd-BOPTA demonstrates that GdL is a better intracellular contrast agent.

Figure 17:
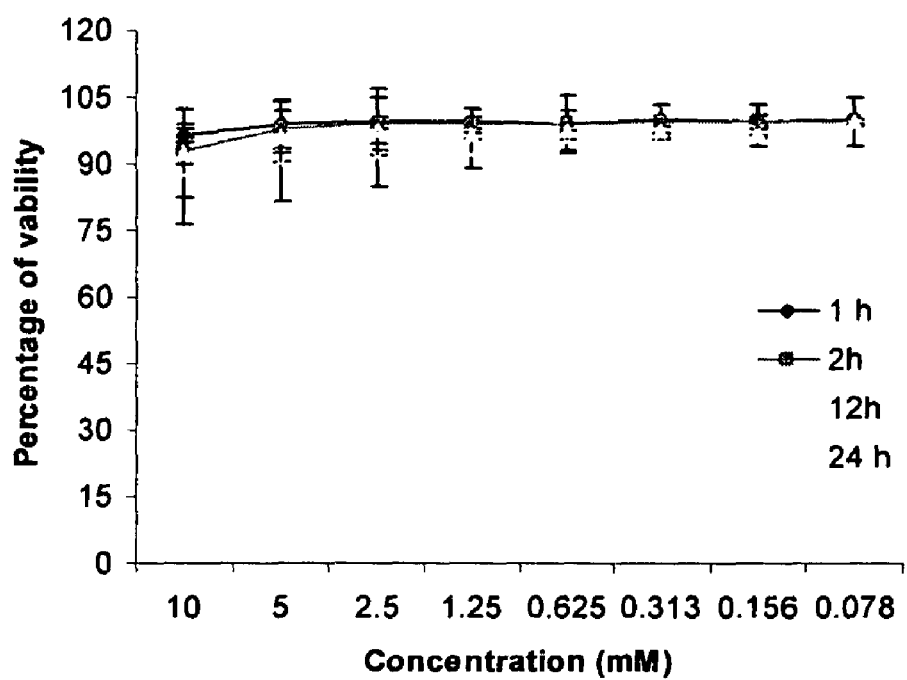
FIG. 17 shows the percentage viability verse dosage of GdL after 1, 2, 12, and 24 hrs of incubation respectively.

As hepatocellular uptake accumulates the contrast agents in cells, the in vitro toxicity is measured via MTT assay using MIHA cell line as shown in FIG. 17. In the MTT assay study, the viability of the cell maintained above 90%, with concentrations of GdL ranging from 0.08 to 10 mM and at different incubation time. The viability was not affected and was satisfactorily high even at high concentration and long incubation time. The MTT assay provided further evidence of the low toxicity of GdL.

In conclusion, GdL is a mono aqua octadentate complex with adamantane that shows excellent hepatic intensity enhancement. Its relaxivity is the highest among the clinical contrast agents (5.96 $mM^{-1}$ $s^{-1}$), and the maximum in vivo liver enhancement of 95% appears shortly after administration. There is a 23% signal improvement as compared with Gd-BOPTA and the half life is 4 times longer, with a higher intensity enhancement in the delay phase. The overall in vivo performance is better than that of Gd-BOPTA, which can be attributed to GdL having a larger amount of hepatocellular uptake. This type of hepatic pathway shows no in vitro toxicity and no in vivo toxicity in rats, and GdL possess a high thermodynamic stability.

THE EXAMPLES

The following examples further illustrate and exemplify the invention, but are in no way intended to limit its scope.

General Experiment

All reactions were performed under nitrogen atmosphere and all solvents were AR grade. Dichloromethane, dimethylformamide, and acetonitrile were distilled from calcium hydride and methanol was distilled from magnesium powder. All solvents were stored over 4 Å molecular sieves. Pyridine was distilled after standing with calcium hydride and stored over sodium hydroxide. Reactions were monitored by thin-layer chromatography (TLC) using 0.25-mm E. Merck pre-coated aluminum oxide plates or silica plates 60, visualizing in iodine atmosphere. Flash chromatography was carried out on aluminum oxide 90 active neutral (particle size 70-230 mesh) or silica gel 60 (particle size 70-230 mesh) support. Yields refer to chromatographically and spectroscopically pure compounds unless otherwise stated. $^1$H NMR spectra were recorded on an AV400 Bruker FT-NMR spectrometer, and ESI-MS spectra were recorded by a LCQ quadrupole ion trap mass spectrometer with methanol or water as the carrier solvent.

Examples

Synthesis and Characterization of Compounds 1-3, L and GdL

1-Hydroxybis(2-tert-butoxycarbonylamine) (1).

Di-tert-butylbicarbonate (1.94 g, 8.9 mmol) was added to 1,3-diaminopropane (1 g, 11.1 mmol) in 250 mL $CH_3CN$ with continuous stirring for 1 h at room temperature. After filtering out the white precipitate and evaporation, the product was purified by silica gel chromatography with eluent $CH_2Cl_2$:MeOH (in 30:1 v:v ratio) and was obtained as a white solid in 90% yield. $^1$H NMR (400 MHz; $CDCl_3$): δ 1.35 (s, 18H), 3.12 (d, 4H), 3.63 (q, 1H). $^{13}$C NMR (400 MHz; $CDCl_3$): δ28.2 ($CH_3$), 43.5 ($CH_2$), 70.3 (CH), 79.5 (C), 156.9 (C). ESI-MS: m/z 290.9 (M+H)$^+$. Anal. Found: C, 53.1; H, 8.8; N, 9.5. $C_{13}H_{26}N_2O_5$ requires C, 53.8; H, 9.0; N., 9.7.

Adamantane-1-carboxylic acid bis-(2-tert-butoxycarbonylamino)-ethylester (2).

Adamantane-1-carbonyl chloride (0.38 g, 1.9 mmol) was dissolved in $CH_2Cl_2$ and added to (1) (0.5 g, 1.7 mmol) in 80 mL anhydrous $CH_2Cl_2$ with pyridine at 60° C. for 12 h. After evaporation of the solvent, 0.1M HCl was added to the mixture and extracted with $CH_2Cl_2$. The organic layer was separated and dried with magnesium sulphate, followed by alumina chromatography with eluent $CH_2Cl_2$: $CH_3OH$ (in 45:1 v:v ratio). The product obtained as a white solid in 60% yield. $^1$H NMR (400 MHz; $CDCl_3$): δ 1.45 (s, 18), 1.70 (t, 6H), 1.79 (dd, 6H), 2.01 (s, 3H), 3.32 (m, 4H), 5.10 (m, 1H). $^{13}$C NMR (400 MHz; $CDCl_3$): δ 28.2 ($CH_3$), 36.3 (CH), 36.6 ($CH_2$), 36.6 ($CH_2$), 37.3 (C), 40.09 ($CH_2$), 71.2 (CH), 79.5 (C), 156.9 (C), 176.9 (C). ESI-MS: m/z 475.3 (M+Na)$^+$. Anal. Found: C, 62.9; H, 8.1; N, 6.0. $C_{24}H_{40}N_2O_6$ requires C, 63.7; H, 8.8; N, 6.2.

Single crystal X-ray analysis of Adamantane-1-carboxylic acid bis-(2-tert-butoxycarbonylamino)-ethylester (2).

X-ray quality crystals were obtained by the slow evaporation of 8 ml compound 2 solution in acetonitrile at room temperature for a week. The positions of the hydrogen atoms were generated geometrically (C—H and N—H bond lengths fixed at 0.95 Å), with assigned isotropic displacement parameters, and were made to ride on their respective parent C and N atoms before the final cycle of least-squares refinement. Data collection: SMART; cell refinement: SMART; data reduction: SAINT-Plus; programme used to solve structure: SHELX97; programme used to refine structure: CrystalClear; molecular graphics: ORTEPII; software used to prepare material: Crystal Structure.

| Crystal data | |
|---|---|
| Empirical Formula | $C_{24}H_{40}N_2O_6 \cdot C_2H_3N$ |
| Molecular Weight | $M_r = 493.63$ |
| Crystal Colour, Habit | Colourless, block |
| Crystal Size/mm | 0.20 × 0.23 × 0.46 |
| Crystal System | monoclinic |
| Space Group | $P 2_1/n$ |
| Unit Cell Dimensions | a = 10.616 (2) Å |
| | b = 9.887 (2) Å |
| | c = 28.294 (5) Å |
| | β = 99.44 (1)° |
| $U/Å^3$ | 2929.5 (10) |
| Z | 4 |
| $D_{calc}/g\,cm^{-3}$ | 1.119 |
| F(000) | 1072.00 |
| Diffractometer | Bruker SMART CCD |
| Radiation | Mo Kα radiation |
| | (λ = 0.7107 Å) |
| $\mu(MoK\alpha)/cm^{-1}$ | 0.79 |
| Temperature/K | 298 |
| Reflections collected | 18237 |
| Unique Reflections | 6901 |
| Observed Reflections [I > 2σ(I)] | 3654 |
| Refinement Method | Full-matrix least-squares on F |
| Weighting Scheme | $w = 1/[\sigma^2(F_0) + (PF_0)^2]$ |
| R | 0.061 |
| $R_w$ | 0.068 |
| Goodness of Fit | 1.037 |
| Maximum Δ/σ | 0.002 |
| No. of parameters | 365 |
| Residual Electron Density/e Å$^{-3}$ | −0.28 to 0.38 |

Adamantane-1-carboxylic acid bis(2-amino)ethylester (3).

To a solution of (2) (0.5 g, 1.1 mmol) in $CH_2Cl_2$, 20% trifluoroacetic acid was added. The reaction mixture was stirred under nitrogen for 10 h at room temperature and then evaporated to give the respective diamine as a white solid in 80% yield. $^1$H NMR (400 MHz; $CD_3OD$): δ 1.69 (t, 6H), 1.79 (dd, 6H), 2.01 (s, 3H), 3.19 (m, 4H), 5.12 (m, 1H). $^{13}$C NMR (400 MHz; $CD_3OD$): δ37.3 (CH), 37.6 ($CH_2$), 39.4 ($CH_2$), 40.1 (C), 41.6 ($CH_2$), 69.2 (CH), 176.9 (C). ESI-MS: m/z 253.3 $(M+H)^+$. Anal. Found: C, 66.2; H, 8.9; N, 11.0. $C_{14}H_{24}N_2O_2$ requires C, 66.7; H, 9.5; N, 11.1.

Adamantane-1-carboxylic acid 4,7,10-tris(carboxylmethyl)-2,12-dioxo-1,4,7,10,13-pentaazacyclohexadecylester (L) DTPA-PNAD.

1,5-diazobicyclo[4.3.0]nonene and (3) (1.45 g, 5.8 mmol) were dissolved in 180 mL DMF, which was added dropwise to DTPA bis(anhydride) (2.05 g, 5.6 mmol) in 250 mL DMF with continuous stirring for 24 h at ambient temperature. The solvent was evaporated under reduced pressure, followed by recrystallization from methanol and diethylether (in 1:2 v:v ratio) to give L as a pale yellow crystalline solid in 65% yield.

$^1$H NMR (400 MHz; $CD_3OD$): δ 2.01 (t, 6H), 2.19 (dd, 6H), 2.28 (s, 3H), 3.01 (s, 2H), 3.12 (s, 4H), 3.31 (s, 4H), 3.49 (t, 4H), 3.79 (t, 4H), 3.95 (m, 4H), 5.12 (m, 1H). $^{13}$C NMR (400 MHz; $CD_3OD$): δ 19.6 ($CH_2$), 19.7 ($CH_2$), 29.4 ($CH_2$), 30.9 ($CH_2$), 31.2 ($CH_2$), 37.3 (CH), 37.6 ($CH_2$), 39.4 ($CH_2$), 40.1 (C), 41.6 ($CH_2$), 69.2 (CH), 176.9 (C). ESI-MS: m/z 610.3 $(M+H)^+$. Anal. Found: C, 55.0; H, 6.8; N, 11.3. $C_{28}H_{43}N_5O_{10}$ requires C, 55.2; H, 7.1; N, 11.5.

Gadolinium adamantane-1-carboxylic acid 4,7,10-tris(carboxylmethyl)-2,12-dioxo-1,4,7,10,13-pentaazacyclohexadecylester (GdL).

The Gd(III) complexes were prepared by a reaction between L (1 g, 1.6 mmol) and an excess of $Gd_2(CO_3)_3$ in $H_2O$ at 65° C. for 24 h. The unreacted carbonate was removed by filtration with celite. The products were precipitated from a mixture of methanol and tetrahydrofuran (in 2:1 v:v ratio) in 90% yield. ESI-MS: m/z 767.3 $(M+H)^+$. Anal. Found: C, 44.6; H, 5.5; N, 9.1. $C_{28}H_{40}N_5O_{10}Gd$ requires, C, 44.0; H, 5.2; N, 9.2.

Relaxometric Measurements

NMRD profiles measure the longitudinal water proton relaxation rate as a function of magnetic fields. Measurements were performed by a Spinmaster FFC fast field cycling NMR relaxometer that covered a continuum of magnetic fields from 0.00024 to 0.47 T. The temperature was controlled by circulating Freon from an external bath and measured by a thermometer that was inserted into the Freon close to the sample. The relaxometer worked under complete control with the reproducibility of the measured $T_1$ values estimated to be ±2%. The NMRD profiles were acquired for a 1-2 mM solution of the complex. Xylenol orange test was employed to check the absence of free Gd(III).

Variable-temperature $^{17}$O NMR measurements were recorded on a JEOL EX-90 (2.1 T) spectrometer that was equipped with a 5 mm probe, using $D_2O$ for external lock of the magnetic field. Experimental settings were spectral width 10000 Hz, pulse width 7 μs, acquisition time 10 ms, 1000 scans, and no sample spinning. The solution used contained $^{17}$O enriched water (2.6%, Yeda, Israel). The observed transverse relaxation rate ($R^O_{2obs}$) was calculated from the line width of the resonance at half height ($\Delta v_{1/2}$): $R^O_{2obs} = \pi \Delta v_{1/2}$.

In Vivo MRI Scan

In a typical experiment, three male Sprague-Dawley (SD) rats (150-200 g) were anesthetized by urethane (10%, 10 mL $kg^{-1}$) through intraperitoneal injection, positioned supine and fixed to a polystyrene cradle with adhesive tape to minimize respiratory motion. After performing a non-enhanced MRI scan, 0.1 mmol $kg^{-1}$ of the Gd(III) complexes in saline was administered via the femoral vein, followed by an immediate scan after the injection. The MRI signal intensity enhancement was monitored up to 180 min and scanned every 4 min. Axial imaging of a 2 mm slice thickness was acquired by the multi-slice and multi-echo (MSME) technique using TR=500 ms, TE=15 ms, and four averages scans. A field of view of 5×5 $cm^2$ and a data matrix of 128×256 were employed. A water tube was placed in the field of view as a phantom reference. Thus intensity enhancement (IE) of region of interest (ROI) at time t is expressed by:

$$IE = 100 \times \frac{ROI_t - ROI_0}{ROI_0}.$$

The half lifetime ($t_{1/2}$) can be calculated in the following equation by assuming that the uptake and excretion of the contrast agents follow a simplified 1st order reaction.

$$IE_t = IE_{max} \times \left(1 - e^{-\frac{t}{t_{1/2}}}\right)$$

Hepatocellular Uptake

The non-tumorigenic immortalized liver cell line (MIHA) (kindly provided by Dr J. R. Chowdhury at the Albert Einstein College of Medicine, New York) was grown in a 96-well plate (polystyrene, flat bottom tissue-culture treated, black with clear bottom) with Dulbecco's modified Eagle's medium (DMEM with 4 mM L-glutamine modified to contain 4.5 g l$^{-1}$ glucose and 1.5 g l$^{-1}$ sodium bicarbonate) containing 10% Bovine Calf Serum (BCS) in a 5% carbon dioxide incubator. Cells were incubated with GdL or Gd-BOPTA for 1 h at 37° C. with concentrations of 0.01, 0.1, 0.5, 5, and 10 mM in modified DMEM containing 10% BCS in a 5% carbon dioxide incubator. At the end of the incubation period, the medium was removed, and the cells were rinsed three times with Dulbecco's phosphate buffered saline (DPBS w/o calcium and magnesium) at ambient temperature. The cells were exposed to 100 µl of 0.25% trypsin and harvested, then counted by hemacytometer. The trypsin/cell suspensions were incubated with concentrated nitric acid 69.5% trace element at 80° C. for 4 h. The dissolved cells were diluted to 5 ml. The final cell solutions were in 3% nitric acid with 5 ppb indium as an internal standard. Gadolinium standard solutions were prepared at 10, 20, 50, 80, and 90 ppb with 5 ppb In using GdCl$_3$. The samples were analyzed by Agilent 7500a ICP-MS with ICP-MS Top installed.

In Vitro Toxicity Assay (MTT Assay)

The non-tumorigenic immortalized liver cell line (MIHA) was maintained in Chee's medium (Gibco BRL) that was supplemented with 5% foetal bovine serum, 100 units mL$^{-1}$ penicillin, 100 mg mL$^{-1}$ streptomycin, 2 mmol L$^{-1}$ L-glutamine, 50 mmol L$^{-1}$ dexamethasone, and 20 mU mL$^{-1}$ recombinant insulin (Boehringer Mannheim, Indianapolis, Ind.). Cells were plated in 96-well plates in the growth medium; the number of cells in each well was 2×10$^4$. The cells were incubated for 24 h in incubator (37° C., 5% CO$_2$). The culture medium was then removed and 100 µl of the growth medium containing the Gd(III) complex was added. After 48 h incubation, 20 µl of the MTT solution (5.0 mg ml$^{-1}$) was added and then incubated for 4 h. The cells were washed with 3% foetal calf serum and were shaken with phosphate buffer saline for 30 min at room temperature. The optical densities (OD$_{570}$) were measured at 570 nm with a DG-3022 a ELISA-Reader and expressed as a percentage relative to control (no gadolinium complex) cells.

Protonation Constants and Formation Constants Measurements

Chemicals

Potassium chloride, potassium hydroxide, tris(hydroxymethyl) aminomethane, potassium hydrogen phthalate, and ethylenediaminetetraacetic acid disodium salt dihydrate were of reagent ACS grade. Anhydrous gadolinium chloride and buffer solutions of pH 4.00 and pH 7.00 were purchased from Aldrich Chemical Company. All titrant solutions were prepared using distilled water that was further purified by passing through a Millipore Milli-Q reverse-osmosis cartridge system (resistivity=18 MΩ cm). The water was degassed by boiling for an hour while argon was purged.

Potentiometric Titrations

The potentiometric titrations were performed with an automatic titration system (Mettler Toledo DL 53). The autotitrating system consisted of a combined pH glass electrode (3 M KCl, AgCl sat.), a Mettler Toledo digital autoburette, and a temperature sensor. Carbonate-free 0.1 M KOH was prepared and standardized by titrating against potassium hydrogen phthalate (KHP). 0.1 M HCl was prepared and standardized by titrating against tris(hydroxymethyl)aminomethane. The combined pH glass electrode was calibrated in hydrogen ion concentration units (p[H]=−log [H$^+$]) by titrating 4.000 ml of standardized HCl that was diluted in 50 ml of 0.1 M KCl with standardized KOH. All solutions were maintained at constant ionic strength (0.1 M KCl), under an argon atmosphere and at constant temperature (25.0±0.1° C.), by using a glass-jacketed titration vessel that was fitted with a thermostated water bath (Techne, refrigerated bath RB-5A, Tempette, Heating system TE-8D). The hydrogen ion concentrations were obtained from the measured pH values by the method of Martell et al. (pK$_w$=13.78) (Martell et al., *Determination and use of stability constants*, 2nd ed., VCH, New York, 1992).

A computer with titration software (DL Win Plus Mettler Toledo) controlled the whole system. Three measurements (about 100 data points each) were performed for each system in the pH range 2.0-12 for ligand protonation and 2.5-10.5 for the complexation experiments. In the complexation reactions of Gd(III) with the ligands, the formation constants were determined by competitive titrations with EDTA disodium salt dihydrate as a competing ligand. The titration mixtures were in a ratio of 1:1:1 of Gd(III), ligand, and EDTA. The standard electrode potential E$^0$, the concentration of KOH solution, and K$_w$ were determined before and after each experiment by the titration of a known amount of HCl, in 0.1 mol-dm$^{-3}$ KNO$_3$ with KOH.

The overall protonation constants and the formation constants of the complexes were determined by the HYPERQUAD programme. The protonation constants were introduced as fixed values in the refinement of the formation constants of the complexes.

Computation

HYPERQUAD is a common computer programme for the calculation of both potentiometric and spectrophotometric data. It uses a least-squares approach and the Gauss-Newton-Marquardt algorithm to refine the constants to give a close approximation of the equilibrium curve. The protonation constants and the complex formation constants were determined by this programme from the potentiometric data. The input file consisted of the components and their concentrations, the initial estimates of the equilibrium constant for each species, the keys to indicate refinable quantities, and the potentiometric equilibrium data that was determined experimentally. The programme set up simultaneous mass-balance equations using the Newton-Raphson method for all of the components that were present at each increment of base added and, with initial assumptions for the equilibrium constants, solved the concentration of each, which varied automatically to effect a minimization in the sum of the squares of differences between the calculated and observed values of −log [H$^+$], thus giving a close approximation of the original potentiometric equilibrium curve, the concentrations of the individual solution species at each data point, and the associated equilibrium constants for metal chelate formation, protonation, and deprotonation. The fitness of the curves is governed by both the chi-squared value at 95% confidence interval and the sigma value. All of the data were obtained with a chi-squared value<12.6 and a sigma value 1±0.05.

Out-of-Cell Experiments

Ten individual solutions that corresponded to single points of conventional titrations were stored in a thermostat at 298±0.1 K, and their pH was checked at 10-min intervals for 1-3 h to ensure the achievement of equilibrium conditions.

REFERENCES

Several publications are referenced hereinabove. The disclosures of these publications are hereby incorporated herein by reference in their entirety, unless otherwise noted.

What is claimed is:

1. A compound having the following structure:

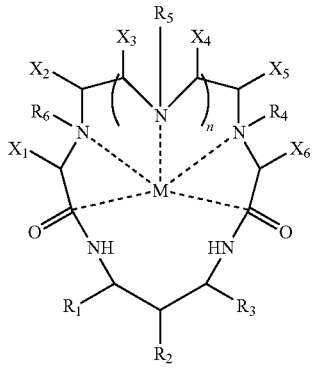

wherein M is a paramagnetic metal ion; only one of $R_1$-$R_3$ comprises an adamantane compound, and $R_4$-$R_6$ are the chelating groups $CH_2COO^-$, $-CH_2COO-$, $-CH_2CONH-$, $-CH_2COC-$, $-CH_2OH$, $-CH_2P(O)(OEt)(OH)$, $-CH_2P(O)(OEt)(Ph)$, $CH_2P(O)(OEt)\{CH_2N(CH_2Ph)_2\}$ or $-CH_2O-$; $X_1$-$X_6$ each comprise hydrogen, alkyl, aryl, alcohol, amine, amido, nitro, ether, ester, ketone, imino, aldehyde, alkoxy, carbonyl, halogen, sulfur containing moieties, phosphorous containing moieties, silicon containing moieties, or other blocking moieties, or together with an adjacent X group are alkyl or aryl groups; n=0-3; monosubstituted or trisubstituted adamantane modifications comprise hydrogen, alkyl, aryl, alcohol, amine, nitro, ether, ester, ketone, imino, aldehyde, alkoxy, carbonyl, halogen, sulfur containing moieties, phosphorous containing moieties, silicon containing moieties; and either one water molecules are directly coordinated with the paramagnetic metal ion.

2. The compound of claim 1, wherein the paramagnetic metal ion is chromium(III), manganese(II), iron(II), iron(III), cobalt(II), nickel(II), copper(II), zinc(II), praseodymium (III), neodymium(III), samarium(III), europium(III), gadolinium(III), terbium(III), dysprosium(III), holmium(III), erbium(III), thulium(III), ytterbium(III), or a combination thereof.

3. The compound of claim 2, wherein the paramagnetic metal ion is gadolinium (III).

4. The compound of claim 1, wherein the macrocyclic chelator is 4,7,10-tris(carboxylmethyl)-2,12-dioxo-1, 4, 7, 10, 14-pentaazacylcohexadecylester.

5. The compound of claim 1, wherein the adamantane compound is connected to a metal chelator with alkyl, allyl, alkyne, aryl, amide, ester, ether, ketone, imino group, phosphorous containing moieties, sulfur containing moieties, silicon containing moieties, ethylene glycol, polyethylene glycol, peptide, or polypeptide.

6. A compound having the following structure:

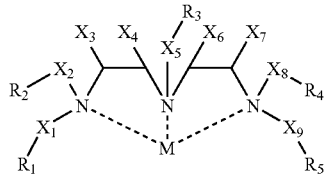

wherein, M is a paramagnetic metal ion; one of $R_1X_1$, $R_2X_2$, $R_3X_5$, $R_4X_8$, $R_5X_9$ form an adamantane compound, and the remaining are the chelating groups $-CH_2COO^-$, $-CH_2COO-$, $-CH_2CONH-$, $-CH_2COC-$, $-CH_2OH$, $-CH_2P(O)(OEt)(OH)$, $-CH_2P(O)(OEt)(Ph)$, $-CH_2P(O)(OEt)\{CH_2N(CH_2Ph)_2\}$ or $-CH_2O-$; $X_1$-$X_9$ each comprise hydrogen, alkyl, aryl, alcohol, amine, amido, nitro, ether, ester, ketone, imino, aldehyde, alkoxy, carbonyl, halogen, sulfur containing moieties, phosphorous containing moieties, silicon containing moieties, or other blocking moieties, or together with an adjacent X group are an alkyl or aryl groups; monosubstituted or trisubstituted adamantane modifications comprise hydrogen, alkyl, aryl, alcohol, amine, nitro, ether, ester, ketone, imino, aldehyde, alkoxy, carbonyl, halogen, sulfur containing moieties, phosphorous containing moieties, or silicon containing moieties; and either one or two water molecules are directly coordinated with the paramagnetic metal ion.

7. The compound of claim 6, wherein the paramagnetic metal ion is chromium(III), manganese(II), iron(II), iron(III), cobalt(II), nickel(II), copper(II), zinc(II), praseodymium (III), neodymium(III), samarium(III), europium(III), gadolinium(III), terbium(III), dysprosium(III), holmium(III), erbium(III), thulium(III), ytterbium(III), or a combination thereof.

8. The compound of claim 6, wherein the adamantane compound is connected to a metal chelator with alkyl, allyl, alkyne, aryl, ester, ether, ketone, imino group, phosphorous containing moieties, sulfur containing moieties, silicon containing moieties, ethylene glycol, polyethylene glycol, peptide, or polypeptide.

9. A method of liver imaging, which comprises administering an effective magnetic resonance imaging amount of a compound of claim 1 to a subject, permitting the compound to accumulate at a site of liver parenchyma in the liver of the subject for which an image is desired, and performing a magnetic resonance imaging scan of the site and generating an image therefrom.

10. The method of claim 9, wherein the compound is a magnetic resonance contrast agent that shows significant organ/tissue specificity to the liver.

11. The method of claim 9, wherein maximum liver intensity enhancement is reached a few minutes after the administration of the contrast agent.

12. A method of imaging kidneys in a subject, which comprises administering an effective magnetic imaging amount of the compound of claim 1 to a subject; permitting the compound to accumulate in the kidneys of the subject performing a magnetic resonance imaging scan of the kidneys and generating an image therefrom.

13. The method of claim 12, wherein the compound is a magnetic resonance contrast agent that shows significant organ/tissue specificity to the kidneys.

14. The method of claim 12, wherein the maximum kidney intensity enhancement is reached a few minutes after the administration of the contrast agent.

* * * * *